United States Patent
Keitel

(10) Patent No.: US 11,376,368 B2
(45) Date of Patent: *Jul. 5, 2022

(54) INJECTION DEVICE

(71) Applicant: medmix Switzerland AG, Haag (CH)

(72) Inventor: Joachim Keitel, Esslingen (DE)

(73) Assignee: MEDMIX SWITZERLAND AG, Haag (CH)

( * ) Notice: Subject to any disclaimer, the term of this patent is extended or adjusted under 35 U.S.C. 154(b) by 300 days.

This patent is subject to a terminal disclaimer.

(21) Appl. No.: 16/513,414

(22) Filed: Jul. 16, 2019

(65) Prior Publication Data

US 2019/0336697 A1 Nov. 7, 2019

Related U.S. Application Data

(60) Division of application No. 15/230,320, filed on Aug. 5, 2016, now Pat. No. 10,413,674, which is a (Continued)

(30) Foreign Application Priority Data

Feb. 5, 2014 (DE) ..................... 20 2014 001 134.6

(51) Int. Cl.
*A61M 5/315* (2006.01)
*A61M 5/31* (2006.01)
(Continued)

(52) U.S. Cl.
CPC ...... *A61M 5/31551* (2013.01); *A61M 5/3146* (2013.01); *A61M 5/3156* (2013.01);
(Continued)

(58) Field of Classification Search
CPC ............ A61M 5/31551; A61M 5/3146; A61M 5/31585; A61M 5/3156; A61M 2205/582;
(Continued)

(56) References Cited

U.S. PATENT DOCUMENTS 5,114,406 A 5/1992 Gabriel et al.
8,747,367 B2 6/2014 Keitel et al.
(Continued)

FOREIGN PATENT DOCUMENTS

WO 9810813 A1 3/1998
WO 2005046770 A1 5/2005
(Continued)

OTHER PUBLICATIONS

International Search Report dated Apr. 14, 2015 of international application PCT/EP2015/000205 on which this application is based.

*Primary Examiner* — Lauren P Farrar
(74) *Attorney, Agent, or Firm* — Global IP Counselors, LLP

(57) ABSTRACT

An injection device includes a housing, a dosing member held so as to be rotatable and fixed in the housing and an injection sleeve held so as to be rotationally fixed in relation to the housing and displaceable therein. A latching unit of the injection device is configured to act between two components thereof which, during setting of an amount of injection fluid to be dispensed, move relative to one another. A set amount of injection fluid is unequivocally assigned to each relative position of the two components.

10 Claims, 15 Drawing Sheets

Related U.S. Application Data continuation of application No. PCT/EP2015/000205, filed on Feb. 3, 2015.

(51) Int. Cl.
    *A61M 5/24*     (2006.01)
    *A61M 5/20*     (2006.01)

(52) U.S. Cl.
    CPC ........... *A61M 5/31585* (2013.01); *A61M 5/24* (2013.01); *A61M 2005/2026* (2013.01); *A61M 2205/581* (2013.01); *A61M 2205/582* (2013.01)

(58) Field of Classification Search
    CPC .............. A61M 2205/581; A61M 5/24; A61M 2005/2026
    See application file for complete search history.

(56) References Cited

U.S. PATENT DOCUMENTS

| | | |
|---|---|---|
| 9,555,192 B2 | 1/2017 | MacDonald et al. |
| 9,901,681 B2 | 2/2018 | Sweeney et al. |
| 2009/0048561 A1* | 2/2009 | Burren .............. A61M 5/31553 604/135 |

FOREIGN PATENT DOCUMENTS

| | | |
|---|---|---|
| WO | 2009132777 A1 | 11/2009 |
| WO | 2013087574 A1 | 6/2013 |
| WO | 2013117332 A1 | 8/2013 |

* cited by examiner

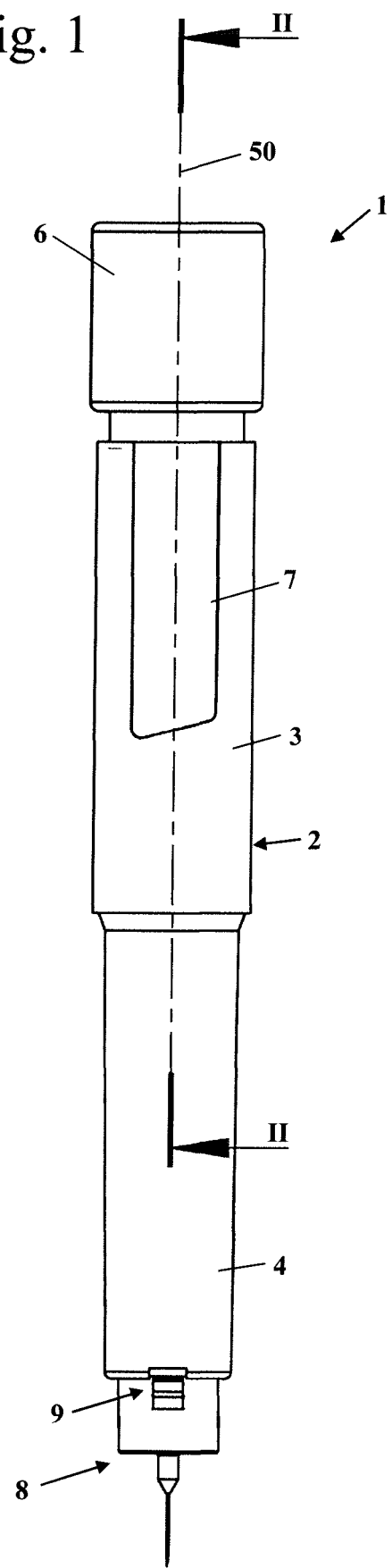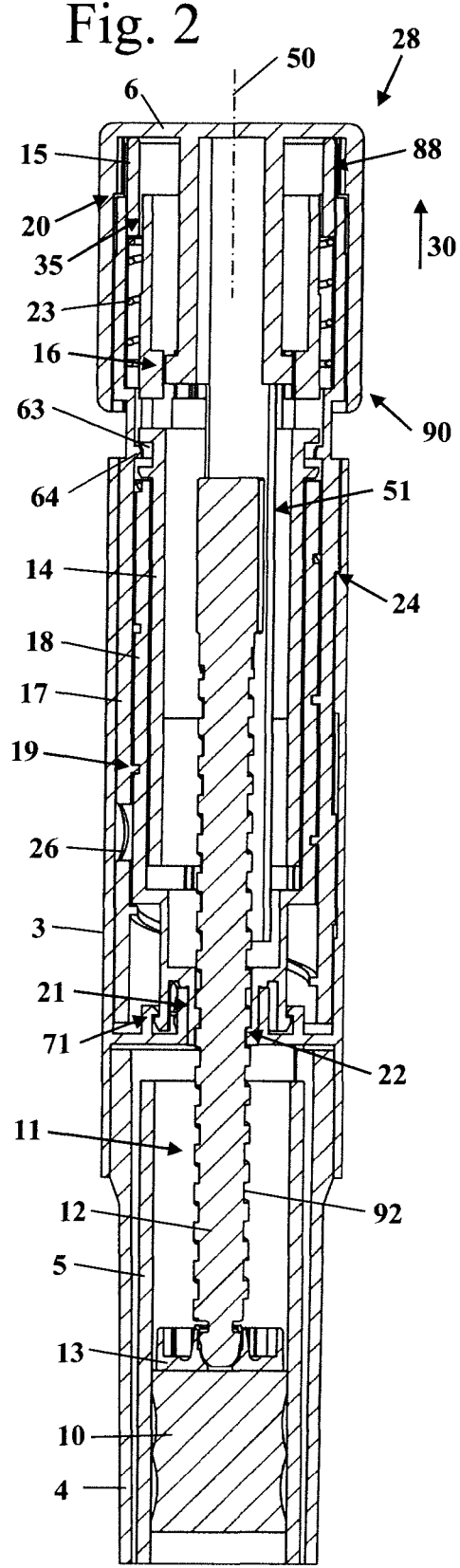

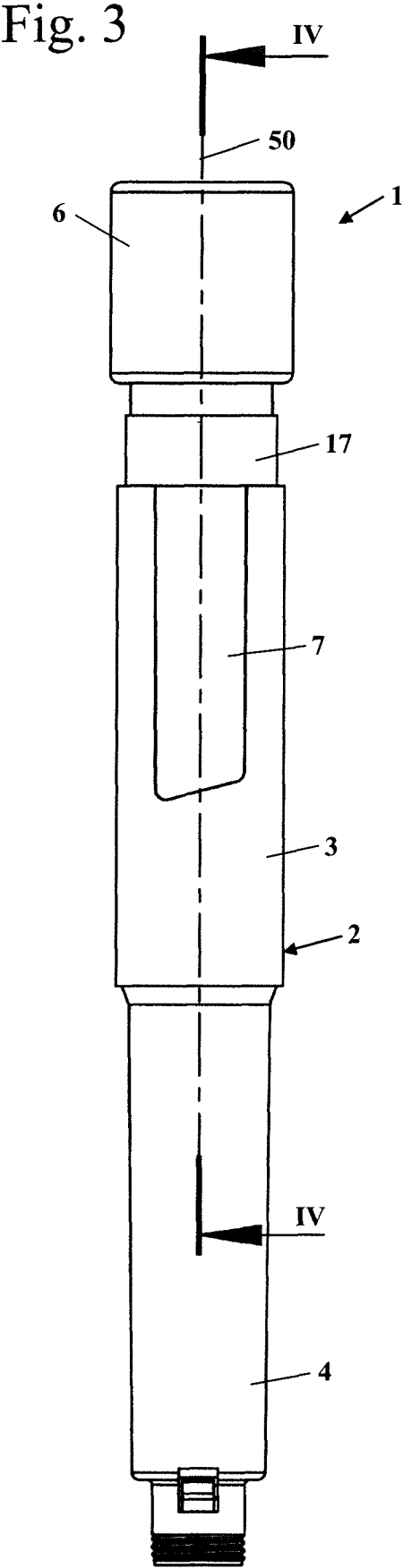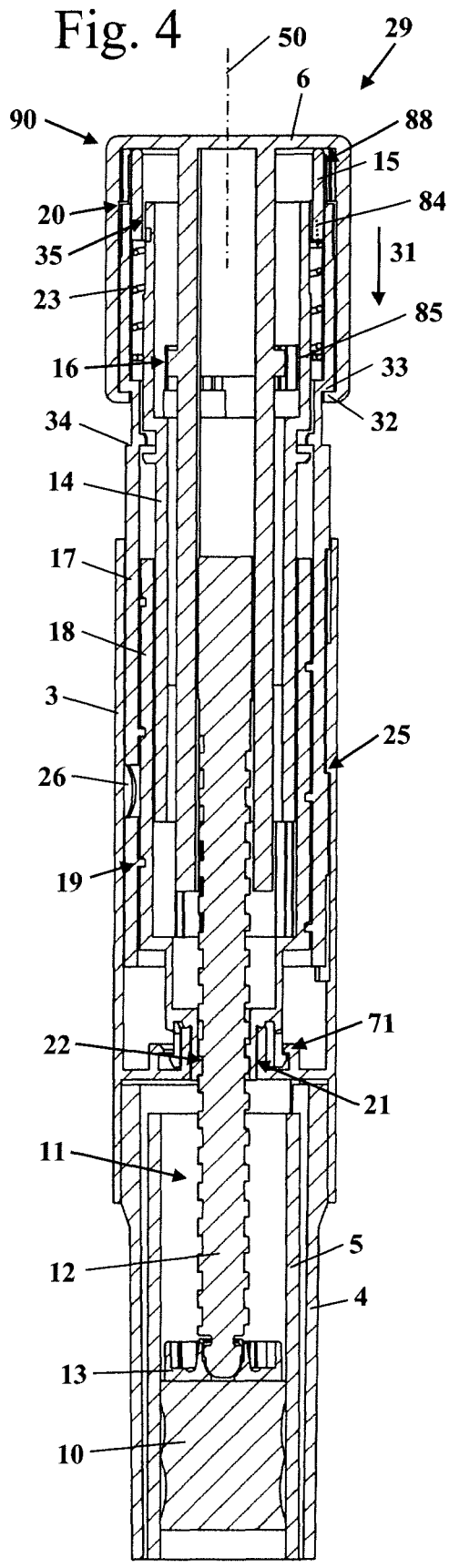

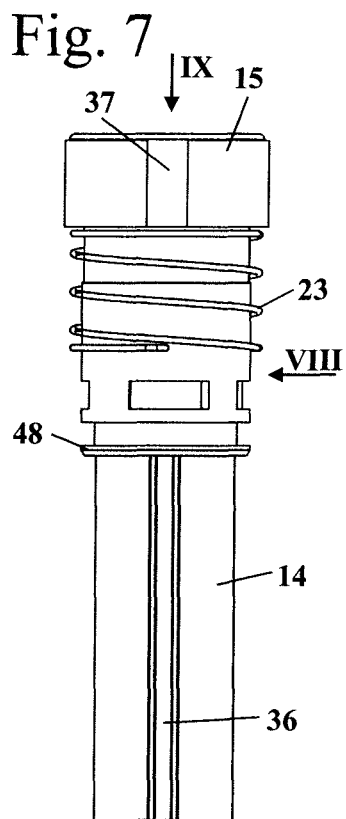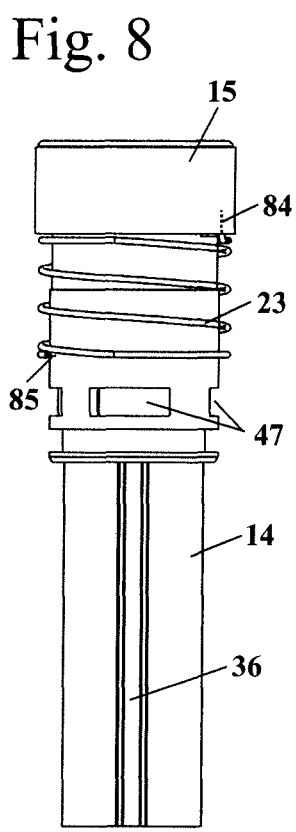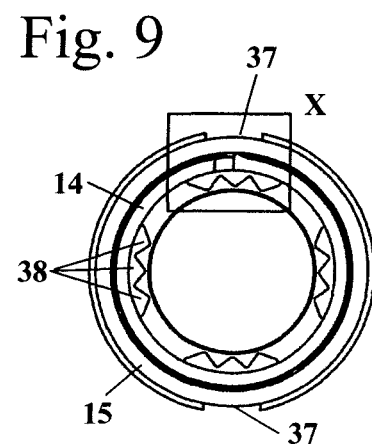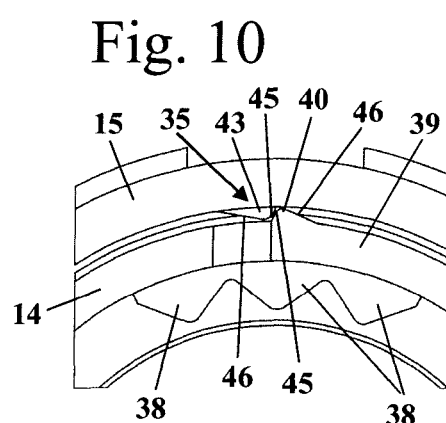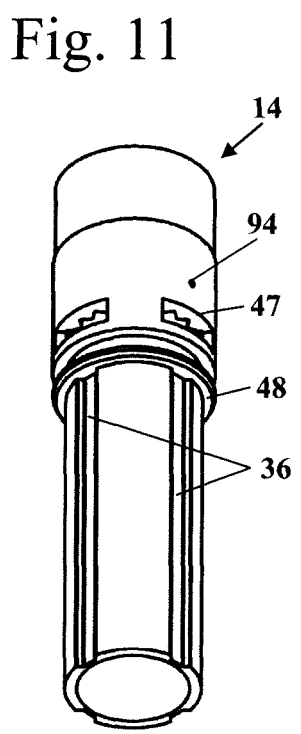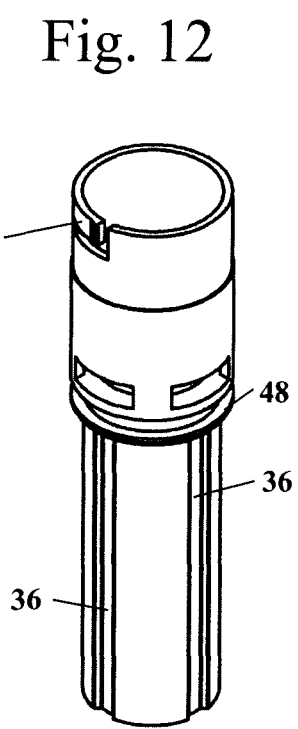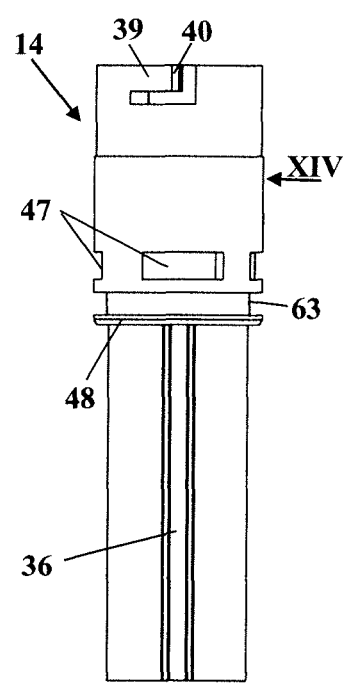

Fig. 14
Fig. 15
Fig. 16
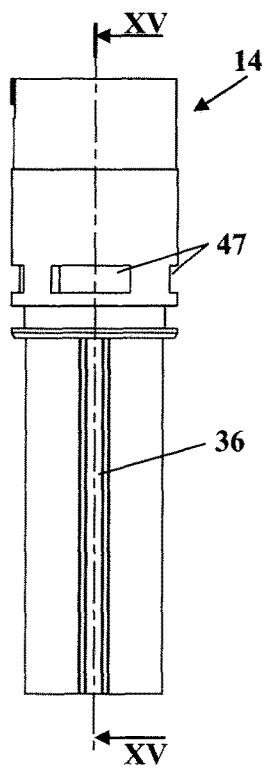
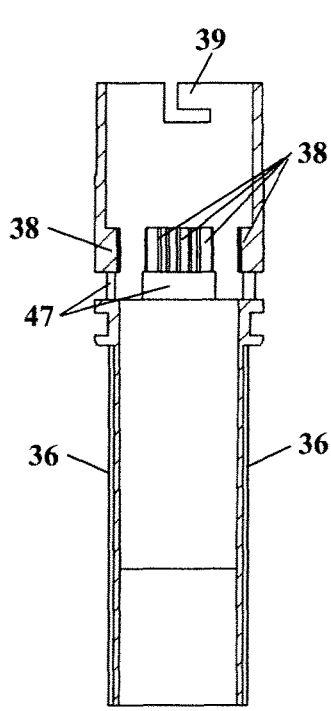
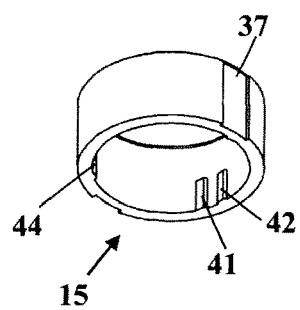
Fig. 17
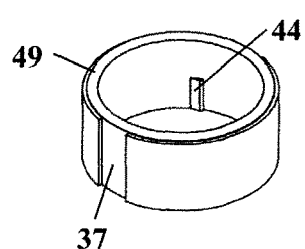
Fig. 18
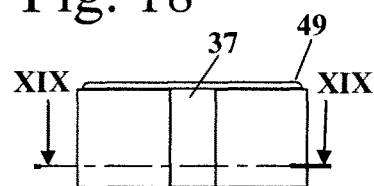
Fig. 20
Fig. 21
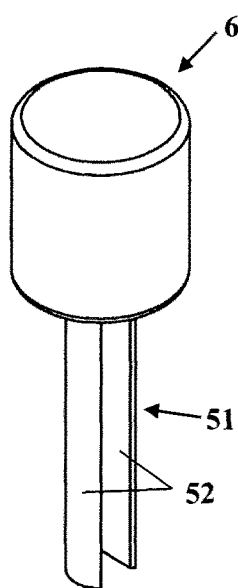
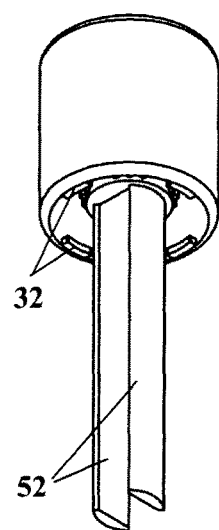
Fig. 19
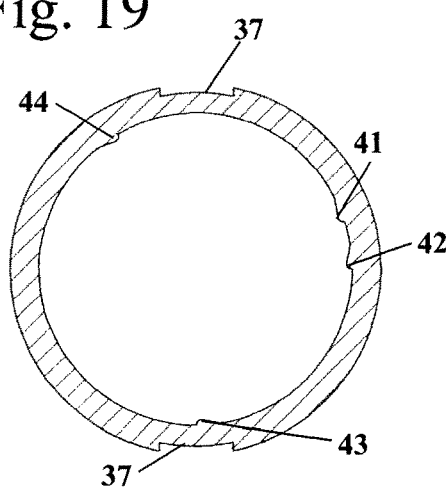

Fig. 22
Fig. 23
Fig. 24
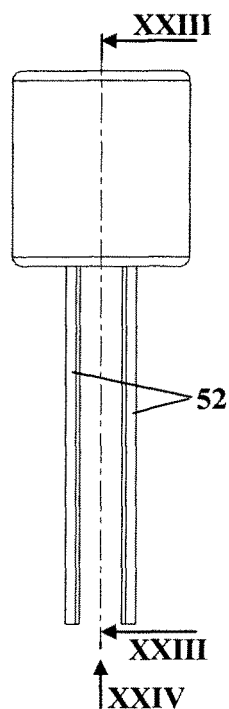
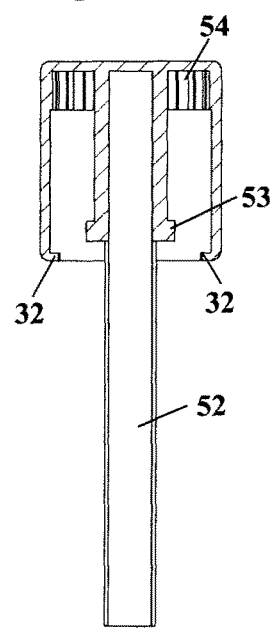
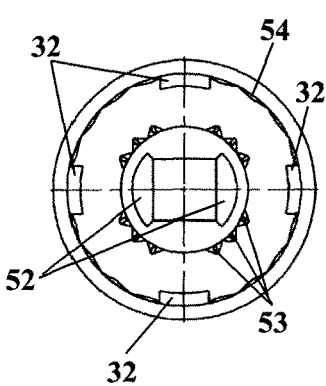
Fig. 25
Fig. 26
Fig. 27
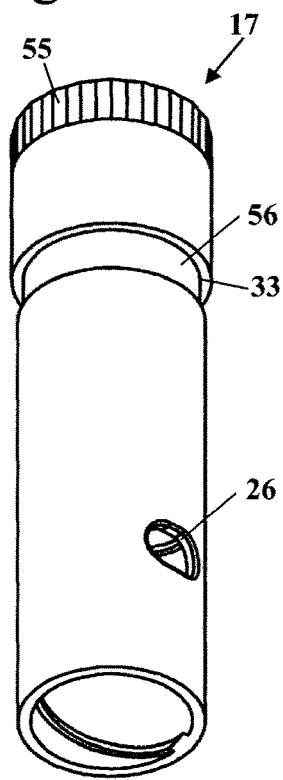
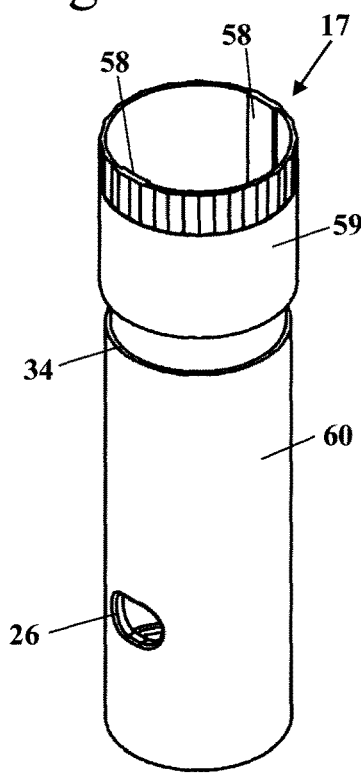
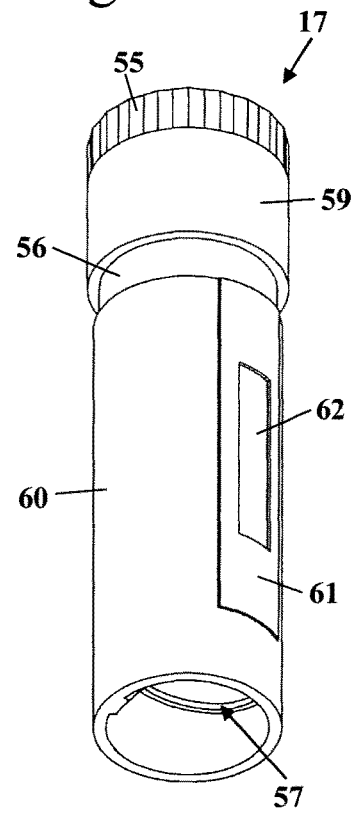

Fig. 40
Fig. 41
Fig. 42
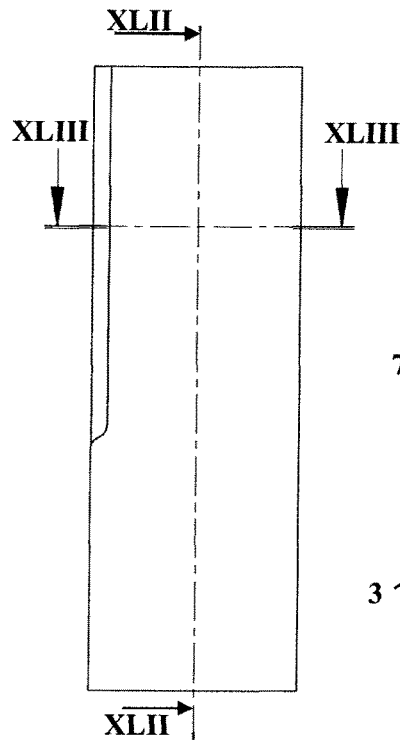
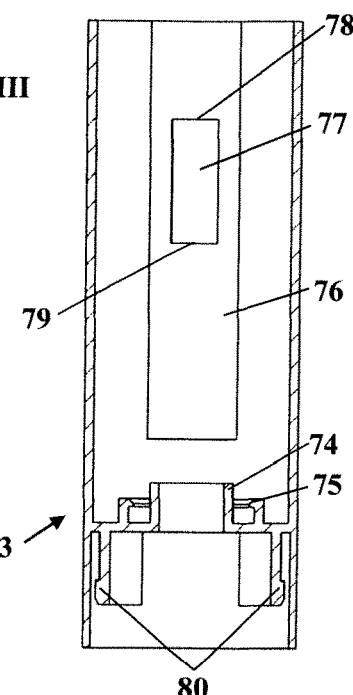
Fig. 43
Fig. 44
Fig. 45
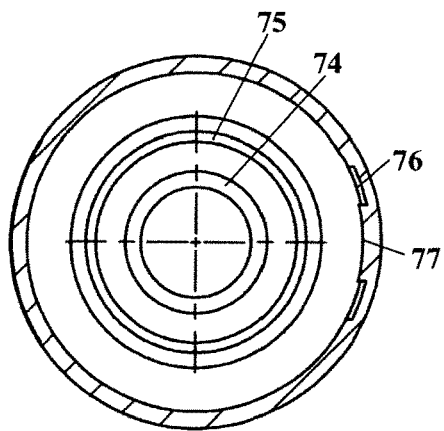
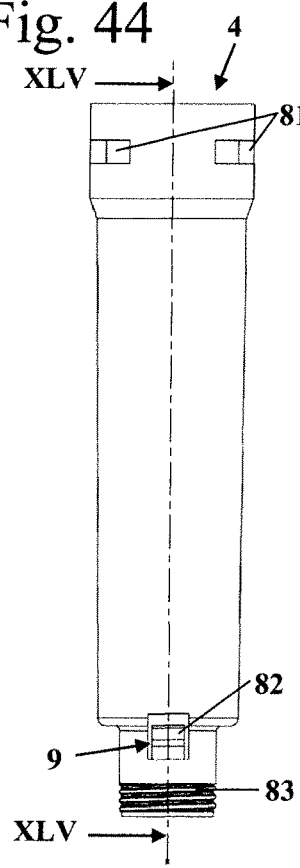
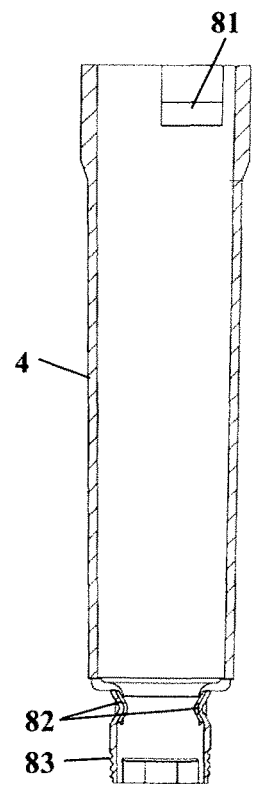

Fig. 59
Fig. 60
Fig. 61
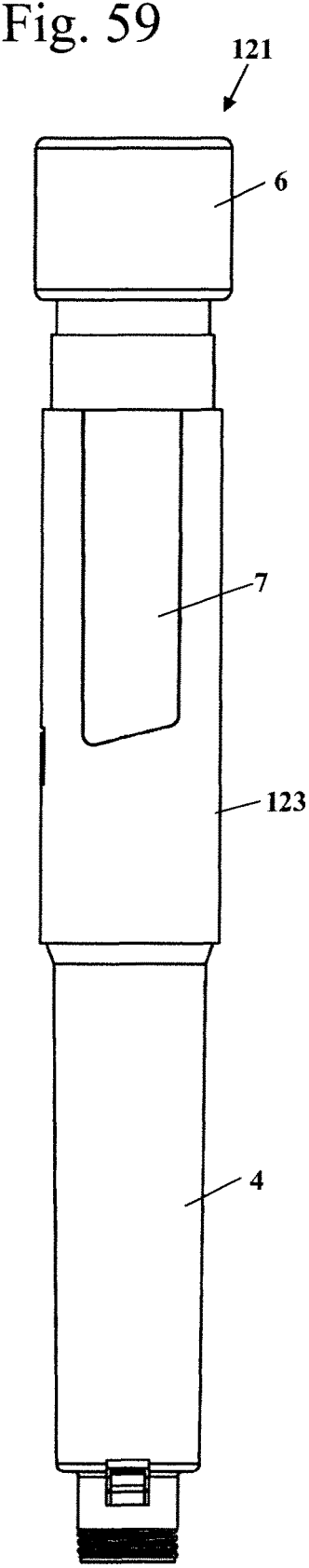
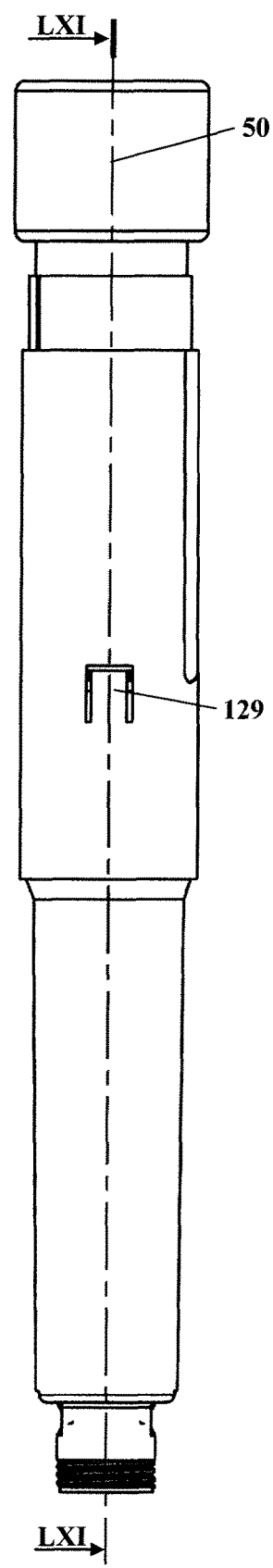
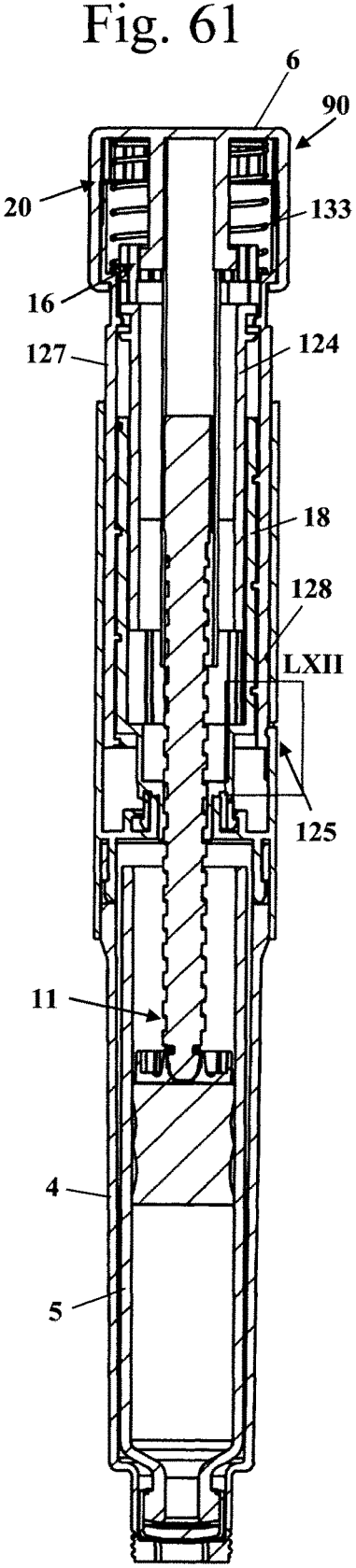

Fig. 67
Fig. 68
Fig. 69
Fig. 70
Fig. 71
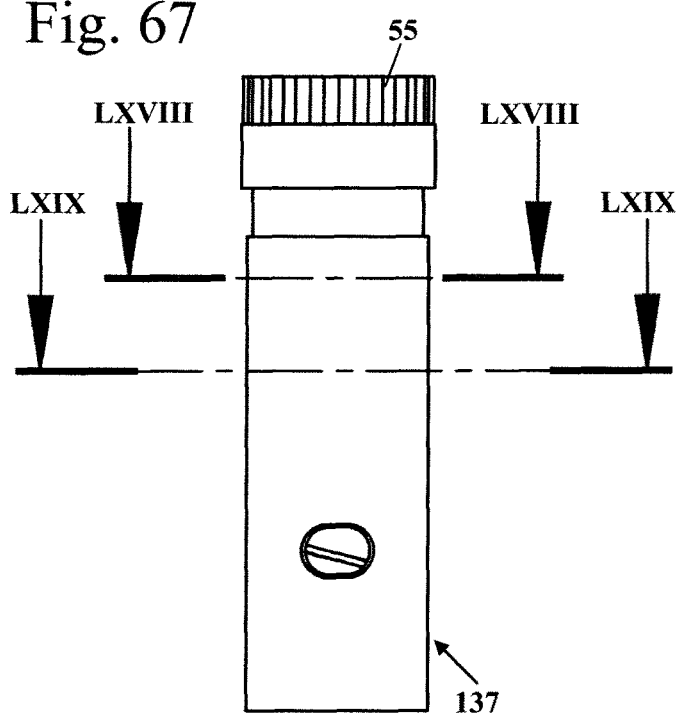
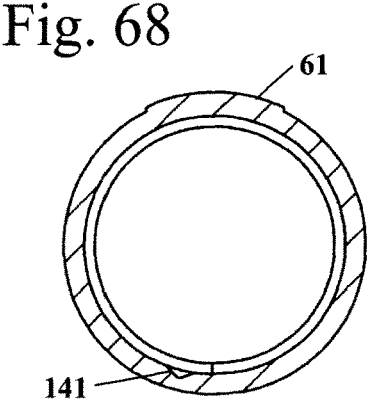
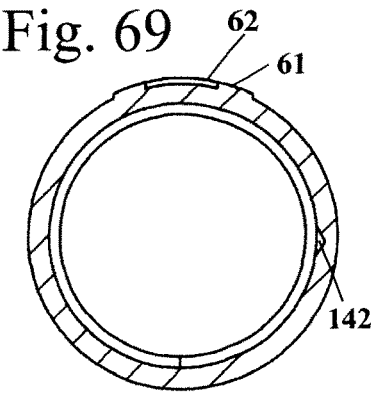
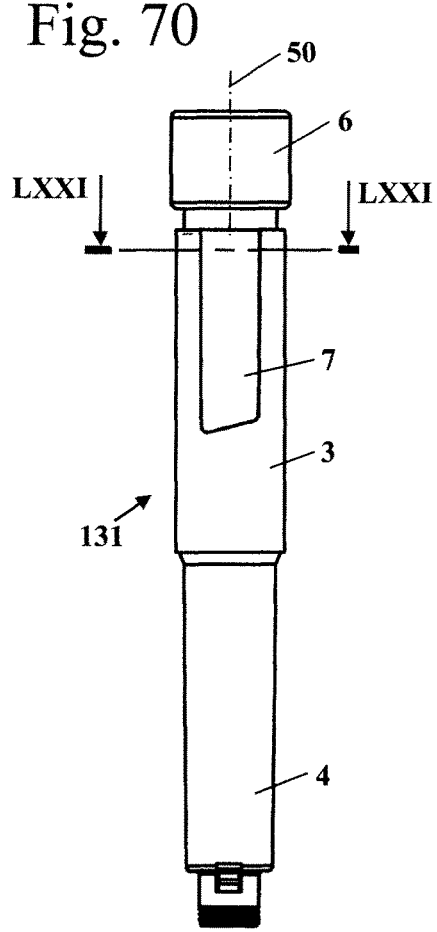
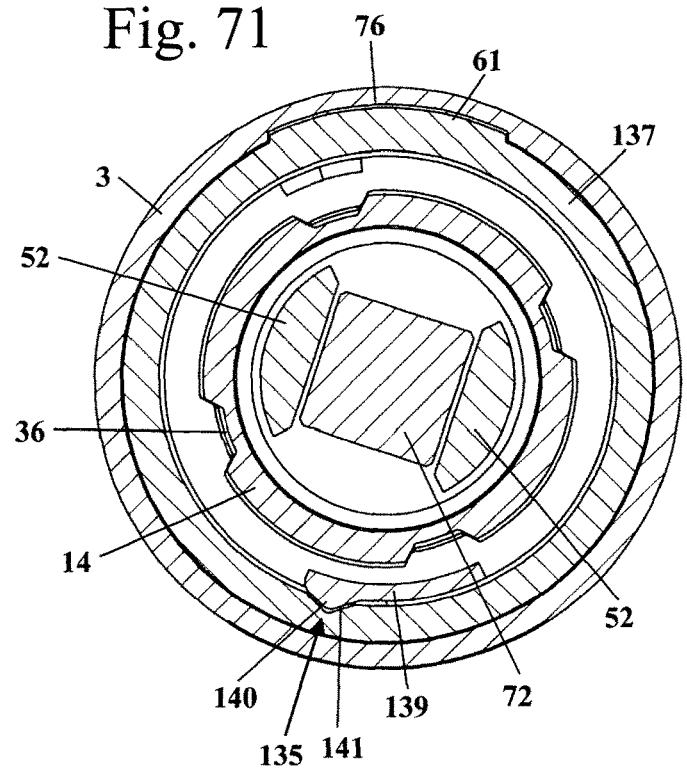

INJECTION DEVICE

CROSS REFERENCE TO RELATED APPLICATIONS

This application is a divisional application of U.S. patent application Ser. No. 15/230,320, filed Aug. 5, 2016, which, in turn, is a continuation application of international patent application PCT/EP2015/000205, filed Feb. 3, 2015, designating the United States and claiming priority from German application 20 2014 001 134.6, filed Feb. 5, 2014, and the entire content of the above applications is incorporated herein by reference.

BACKGROUND OF THE INVENTION

An injection device in which a latching part which is connected in a rotationally fixed manner to the operating button and interacts with the injection sleeve is provided is known from WO 2013/117332 A1. When setting an amount of injection fluid to be squeezed out, the operating button is rotated in relation to the housing, and when the injection fluid is being squeezed out, is held so as to be rotationally fixed in relation to the housing and guided in the longitudinal direction of the injection device. When setting an amount of injection fluid to be squeezed out, and when the injection fluid is being squeezed out of the container, the injection sleeve is moved in the direction of the longitudinal central axis of the injection device, without being rotated in relation to the housing. On account thereof, the rotational position of the operating button in relation to the injection sleeve is modified in the case of each injection procedure.

A second latching installation of WO 2013/117332 A1 acts between a housing part and a dosing member. The dosing member rotates when setting the amount of an injection fluid to be squeezed out, and the dosing member rotates back when the amount of injection fluid to be squeezed out is being squeezed out. The latching installation has two latching arms which are disposed so as to be mutually opposite. Since the dosing member is rotatable about the longitudinal central axis by multiple rotations, each latching position is reached multiple times when setting the maximum dosage.

If and when, for example, amounts of 0.20 ml and 0.25 ml of injection fluid which are to be set for a therapy are required, then known injection devices are conceived such that dosing increments of at most 0.05 ml are settable. This means, on the one hand, that the user has to overcome a plurality of latching steps until the minimum dosage which is provided for the therapy is reached. On the other hand, the amount of injection fluid which has to be discarded during the priming procedure is comparatively sizeable in the case of a minimum fixed dosage increment of 0.05 ml, for example. Therefore, significantly smaller dosing increments would be desirable for the priming procedure. However, this leads to a significantly increased number of latching positions which have to be overcome by the user when setting the dosage.

SUMMARY OF THE INVENTION

It is an object of the invention to provide an injection device which enables a plurality of latching positions to be disposed at variable spacings.

An injection device defines a longitudinal center axis, a proximal direction and a distal direction. The injection device includes: a housing; a dosing member held so as to be rotatable and fixed in the housing in the direction of the longitudinal center axis; an injection sleeve held so as to be rotationally fixed in relation to the housing and displaceable in the direction of the longitudinal center axis; the dosing member being connected to the injection sleeve via a first threaded connection; the dosing member being configured to rotate in a first rotational direction in relation to the housing when an amount of injection fluid to be dispensed is being set; the injection sleeve being configured to move in the distal direction because of the first threaded connection; the dosing member being further configured to rotate in a second rotational direction counter to the first rotational direction when the amount of injection fluid to be dispensed is being pressed out; the injection sleeve being configured to move in the proximal direction because of the first threaded connection; a container configured to contain injection fluid; a dosing piston configured to press injection fluid out of the container; the dosing piston being connected to the dosing member via a second threaded connection; the dosing piston being connected to the dosing member in a rotationally fixed manner so as to rotate conjointly therewith when the amount of injection fluid to be dispensed is being set; the dosing piston being connected to the injection sleeve in a rotationally fixed manner when the amount of injection fluid to be dispensed is pressed out and, by virtue of the second threaded connection, is moved in the proximal direction; a latching unit configured to act at least when the amount of injection fluid to be dispensed is being set; and, the latching unit being configured to act between two components of the injection device which during setting of the amount of injection fluid to be dispensed, move relative to one another, wherein a set amount of injection fluid is unequivocally assigned to each relative mutual position of the two components.

The present invention provides that the latching installation acts between two components of the injection device wherein each relative mutual position of the two components is unequivocally assigned a set amount of injection fluid. On account thereof, the required latching positions may be disposed at variable mutual spacings. For example, an injection device which provides precisely three latching positions at 0.01 ml for the priming procedure, and at 0.20 ml and 0.25 ml for the dosages to be injected, could be provided for the exemplary therapy which has been described at the outset. Operating the injection device is significantly simplified on account thereof. Where reference is made hereunder to "the two components", this means the two components between which the latching installation is in effect and in which case each relative mutual position is unequivocally assigned a set amount of injection fluid.

The latching installation advantageously has at least one latching element and at least one counter-latching element which in a latching position interacts with the latching element.

Advantageously, one of the two components between which the latching installation acts is the dosing member, and the other of the two components is the injection sleeve. When setting the amount of injection fluid to be squeezed out, the dosing member and the injection sleeve are moved in relation to one another in helical manner, since the dosing member performs a rotation movement, and the injection sleeve performs a movement in the direction of the longitudinal central axis of the injection device. When the injection fluid is being squeezed out, the dosing member and the injection sleeve move back from one another to their respective initial position. On account thereof, precisely one set amount of injection fluid is assigned to each relative mutual position of the dosing member and the injection sleeve.

It may also be provided that one of the two components between which the latching installation acts is the injection sleeve, and the other of the two components is the housing. The injection sleeve moves in the direction of the longitudinal central axis of the injection device when setting an amount of injection fluid to be squeezed out. When the injection fluid is being squeezed out, the injection sleeve moves back to the initial position thereof. On account thereof, each axial position of the injection sleeve corresponds to precisely one set amount of injection fluid.

The statement that the latching installation acts between the two components means that the latching installation is effective between these components, but does not mean that the latching element and the counter-latching element have to be disposed on the two components per se. Rather, the latching element and the counter-latching element may be configured on further components which likewise perform the relative mutual movement of the two components and, on account thereof, are effective between the two components.

It is provided that the injection device has an operating element. The operating element advantageously has a distal position in which the operating element is located when setting the amount of injection fluid to be squeezed out, and a proximal position in which the operating element is located when the amount of injection liquid to be squeezed out is being squeezed out. The distal position and the proximal position of the operating element here are positions of the operating element in relation to the injection sleeve. Advantageously, the operating element by way of a first coupling is connectable in a rotationally fixed manner to a follower or entrainer which is connected in a rotationally fixed manner to the dosing member, and by way of a second coupling is connectable to the injection sleeve. In the distal position of the operating element, the operating element by way of the first coupling is advantageously connected in a rotationally fixed manner to the entrainer. The second coupling in the distal position of the operating element is advantageously opened such that the operating element is rotatable in relation to the injection sleeve. In the proximal position of the operating element the first coupling is advantageously opened, and the operating element is rotatable in relation to the entrainer, and the operating element by way of the second coupling is connected in a rotationally fixed manner to the injection sleeve. The operating element is rotated when setting an amount of injection fluid to be set. The entrainer, the dosing member, and the dosing piston which is connected in a rotationally fixed manner to the operating element rotate conjointly with the operating element. When injection fluid is being squeezed out the operating element is connected in a rotationally fixed manner to the injection sleeve and, on account thereof, is guided in a rotationally fixed manner in relation to the housing. The entrainer conjointly with the dosing member rotates about the longitudinal central axis of the injection device, and by way of the second threaded connection moves the dosing piston in the proximal direction. On account thereof, the injection fluid is squeezed out of the container.

Comfortable operation results when the latching installation is effective only when setting the amount of injection fluid to be squeezed out, but not during the injection procedure. This may be achieved in a simple manner in that the latching installation is coupled to the position of the operating element, and is effective in the distal position of the operating element. In the proximal position of the operating element, the at least one latching element and the at least one counter-latching element advantageously are mutually disengaged, independently of the relative mutual position of the two components. If and when the latching installation is effective only when setting an amount of injection fluid to be squeezed out, the latching element and/or the counter-latching element may be configured so as to be asymmetrical such that a significantly higher force is required for overcoming a latching position in order to reduce the set amount of injection fluid to be squeezed out than for setting an amount of injection fluid to be squeezed out.

Advantageously, one of the two components between which the latching installation acts is the entrainer, and the other of the two components is the injection sleeve. A simple construction of the injection device results on account thereof. In the case of injection devices in which the operating element is rotated by fewer than one revolution in order for the maximum dosage to be reached, precisely one set amount of injection fluid is assigned to each relative rotational position of the entrainer and the injection sleeve. Advantageously, the entrainer in the direction of the longitudinal central axis is coupled to the position of the injection sleeve such that the entrainer moves conjointly with the injection sleeve in the distal direction when setting the amount of injection fluid to be squeezed out, and moves in the proximal direction when the set amount of injection fluid is being squeezed out. On account thereof, a simple construction of the first coupling which acts between the entrainer and the operating element is enabled.

A simple construction of the injection device results if and when at least one latching element is disposed on the one of the two components, and at least one counter-latching element is disposed on the other of the two components. In a particularly advantageous manner, the latching element and the counter-latching element, respectively, are configured so as to be integral with the respective component. A fixed connection to the respective component may also be advantageous in particular in order for the production of the component to be simplified.

In order for it to be achieved in a simple manner that the latching installation is effective only when setting an amount of injection fluid to be set, but not when the injection fluid is being squeezed out, it is advantageous for at least one latching element to be disposed on one latching part which is connected in a rotationally fixed manner to one of the two components, so as to be displaceable in relation to this component in the direction of the longitudinal central axis. Advantageously, at least one counter-latching element is disposed on the other of the two components. The at least one latching element in a first axial position of the latching part may advantageously come into engagement with the at least one counter-latching element. The at least one latching element, in a second axial position of the latching part, independently of the relative mutual position of the two components, is advantageously disengaged from the at least one counter-latching element.

A simple construction results when the position of the latching part is linked to the position of the operating element such that the latching part, in the distal position of the operating element, is located in the first axial position thereof and, in the proximal position of the operating element, is located in the second axial position thereof. The latching part is advantageously elastically biased in the direction toward the first axial position thereof, preferably by at least one spring.

A simple construction having a minor number of individual parts results when the latching part has at least one spring arm which biases the latching part in the direction toward the first axial position thereof. The spring arm advantageously is configured so as to be integral with the latching part such that no additional spring is required for biasing the latching part in the direction toward the first axial position thereof.

Advantageously, a spring which biases the dosing member in the second rotation direction acts between the injection sleeve and the dosing member. On account thereof, the dosing member is reset in the direction toward the next latching position which corresponds to the next lowest amount of injection fluid to be set, when the operating element is released between two latching positions. On account thereof, inadvertent squeezing out of an unintended amount of injection fluid is prevented in a simple manner. Since the injection sleeve in relation to the dosing member moves in the direction of the longitudinal central axis when setting an amount of injection fluid to be squeezed out, the spring advantageously is connected to the entrainer which is connected in a rotationally fixed manner to the dosing member. Advantageously, the spring by way of one end is secured to the injection sleeve, and by way of the other end is secured to the entrainer. A simple construction of an injection device which has a latching part results when the spring by way of one end is secured to the latching part, and by way of the other end is secured on the entrainer. A spring which biases the dosing member in the second rotation direction is advantageous in particular in the case of an injection device in which the latching installation thereof is only effective when setting an amount of injection fluid, but not when the latter is being squeezed out. The latching installation advantageously is configured such that to overcome the latching positions a lesser force is required for setting an amount of injection fluid to be squeezed out, than for turning back in the opposite direction. On account thereof, when the operating element is released between two latching positions, it may be ensured that the dosing member is reset only to the next lowest latching position and that this latter latching position cannot be overcome. At the same time, the spring which biases the dosing member in the second rotation direction may be conceived to be so strong that reliable turning back of the dosing member is also ensured in the case of unfavorable friction conditions and tolerances.

BRIEF DESCRIPTION OF THE DRAWINGS

The invention will now be described with reference to the drawings wherein:

FIG. 1 shows a side view of a first embodiment of an injection device in the zero position;

FIG. 2 shows a section along the line II-II in FIG. 1;

FIG. 3 shows a side view of the injection device of FIG. 1, after setting an amount of injection fluid to be squeezed out;

FIG. 4 shows a section along the line IV-IV in FIG. 3;

FIG. 7 shows a side view of the entrainer, the spring, and the latching part of the injection device of FIGS. 1 to 6;

FIG. 8 shows a side view of the assembly in FIG. 7, in the direction of the arrow VIII in FIG. 7;

FIG. 9 shows a plan view in the direction of the arrow IX in FIG. 7;

FIG. 10 shows the fragment X of FIG. 9, in an enlarged illustration;

FIGS. 11 and 12 show perspective illustrations of the entrainer of the injection device of FIGS. 1 to 6;

FIG. 13 shows a side view of the entrainer;

FIG. 14 shows a side view in the direction of the arrow XIV in FIG. 13;

FIG. 15 shows a section along the line XV-XV in FIG. 14;

FIGS. 16 and 17 show perspective illustrations of the latching part of the injection device of FIGS. 1 to 6;

FIG. 18 shows a side view of the latching part of FIGS. 16 and 17;

FIG. 19 shows a section along the line XIX-XIX in FIG. 18;

FIGS. 20 and 21 show perspective illustrations of the operating element of the injection device;

FIG. 22 shows a side view of the operating element;

FIG. 23 shows a section along the line XXIII-XXIII in FIG. 22;

FIG. 24 shows a view of the operating element, in the direction of the arrow XXIV in FIG. 22;

FIGS. 25 to 27 show perspective illustrations of the injection sleeve of the injection device;

FIGS. 40 and 41 show side views of a housing part of the injection device of FIGS. 1 to 6;

FIG. 42 shows a section along the line XLII-XLII in FIG. 41;

FIG. 43 shows a section along the line XLIII-XLIII in FIG. 41;

FIG. 44 shows a side view of a holder of the injection device of FIGS. 1 to 6;

FIG. 45 shows a section along the line XLV-XLV in FIG. 44;

FIGS. 59 and 60 show side views of an embodiment of an injection device after setting an amount of injection fluid to be squeezed out;

FIG. 61 shows a section along the line LXI-LXI in FIG. 60;

FIG. 67 shows a side view of an embodiment of an injection sleeve;

FIG. 68 shows a section along the line LXVIII-LXVIII in FIG. 67;

FIG. 69 shows a section along the line LXIX-LXIX in FIG. 67;

FIG. 70 shows a side view of an injection device in the zero position;

FIG. 71 shows a section along the line LXXI-LXXI in FIG. 70;

DESCRIPTION OF THE PREFERRED EMBODIMENTS OF THE INVENTION

Figure 5:
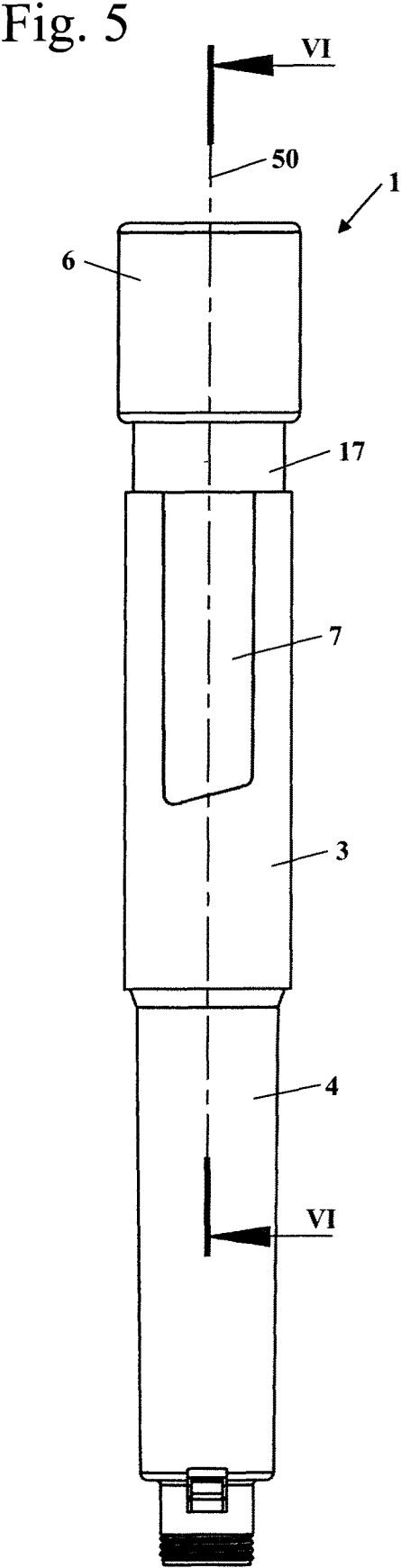
FIG. 5 shows a side view of the injection device of FIG. 1, after setting an amount of injection fluid to be squeezed out and displacing the operating element in the proximal direction.

FIG. 1 shows an injection device 1 which has a housing 2. The housing 2 includes an upper distal housing part 3, and a holder 4 which is disposed on the proximal side of the upper housing part 3. An injection needle 8 is secured to the proximal side of the holder 4. Adjacent to the injection needle 8, the holder 4 has a latching installation 9, a container 5 shown in FIG. 2 being latched thereto in the holder 4. An operating element 6 is disposed on the distal side of the injection device 1. As is shown in FIG. 1, the injection device 1 has a longitudinal central axis 50 which runs in the longitudinal direction of the injection device 1. The upper housing part 3 has a viewing window 7 which is configured so as to be at least partially transparent. The viewing window 7 in FIG. 1 is drawn in a schematic and non-transparent manner such that the components lying therebelow are not visible in FIG. 1.

The distal end of the injection device 1 is that end that faces away from an injection needle 8 which is held on the injection device. "Proximal" refers to that side of the injection device 1 that faces the puncture when injecting, "distal" referring to that side that faces away from the puncture. The proximal direction refers to the direction of injection, that is, the direction toward the injection needle 8, or that direction in which the injection fluid is squeezed out of the container 5, respectively. The distal direction refers to the opposite direction, that is, away from the injection needle 8.

As is shown in FIG. 2, a plug 10, a piston disk 13 of a dosing piston 11 bearing thereon, is disposed in the container 5. The dosing piston 11 moreover includes a piston rod 12 which carries an external thread 92.

An injection sleeve 17, the external side thereof being visible through the viewing window 7 of the upper housing part 3, is disposed in the upper housing part 3. The injection sleeve 17 has an opening 26, the external circumference of a dosing member 18 which is disposed within the injection sleeve 17 being visible therethrough. The dosing member 18, which may also be referred to as a graduated tube, on the external circumference thereof carries a graduation (not visible in FIG. 2) which to the operator is visible through the viewing window 7 and the opening 26.

The injection sleeve 17 in the upper housing part 3 is held so as to be displaceable in the direction of the longitudinal central axis 50 and so as to be rotationally fixed in relation to the upper housing part 3. The dosing member 18 and the injection sleeve 17 are interconnected by way of a first threaded connection 19. An entrainer 14 which is connected in a rotationally fixed manner to the dosing member 18 is disposed within the dosing member 18. The entrainer 14 has a circumferential groove 63, a retaining periphery 64 of the injection sleeve 17 protruding thereinto. The retaining periphery 64 here is held with a clearance in the circumferential groove 63. On account thereof, the injection sleeve 17 and the entrainer 14 are interlinked in the direction of the longitudinal central axis 50. However, by virtue of the clearance, minor relative movement between the injection sleeve 17 and the entrainer 14 in the direction of the longitudinal central axis 50 is possible.

The dosing member 18 by way of a latching connection 71 is held in the upper housing part 3 so as to be fixed in the direction of the longitudinal central axis 50. In the embodiment the latching connection 71 is disposed at the proximal end of the dosing member 18. The dosing member 18 by way of a pivot bearing 21 is rotatably mounted in the upper housing part 3. The dosing member 18 by way of a second threaded connection 22 is connected to the piston rod 12 of the dosing piston 11. The operating element 6 by way of an entrainment portion 51 is connected in a rotationally fixed manner to the piston rod 12.

The operating element 6 in FIG. 2 is shown in the distal position 90 thereof in relation to the injection sleeve 17. The operating element 6 by way of a first coupling 16 is connectable to the entrainer 14. In the distal position 90 of the operating element 6, the operating element 6 and the entrainer 14 are interconnected in a rotationally fixed manner by way of the first coupling 16. A latching part 15 is disposed in the operating element 6. The latching part 15 in the embodiment is configured so as to be annular, being disposed on the external circumference of the entrainer 14. A latching installation 35 which will be described in yet more detail hereunder is formed between the entrainer 14 and the latching part 15. The latching part 15 is connected in a rotationally fixed manner to the injection sleeve 17. The latching part 15 is movable in the direction of the longitudinal central axis 50, being biased by a spring 23 in the direction toward the first axial position 88 of the latching part 15, as shown in FIG. 2.

A second coupling 20 which is opened in the zero position 28 of the injection device 1, as shown in FIG. 2, is provided between the operating element 6 and the injection sleeve 17. On account thereof, the operating element 6 is rotatable in relation to the injection sleeve 17. No dosage is set in the zero position 28. In the zero position 28 the injection sleeve 17 bears on a first stop 24 on the upper housing part 3.

In order for an amount of injection fluid to be squeezed out to be set, the operator rotates the operating element 6 in a first rotation direction, being the clockwise direction in the embodiment. The entrainer 14 and the dosing member 18 which is connected in a rotationally fixed manner to the entrainer 14 are conjointly rotated by way of the first coupling 16. The piston rod 12 is also conjointly rotated by way of the entrainment portion 51 of the operating element 6. The injection sleeve 17, by virtue of the first threaded connection 19 and of the rotationally fixed fixation of the injection sleeve 17 in the upper housing part 3, is moved in the distal direction 30. The entrainer 14 and the operating element 6 also move conjointly with the injection sleeve 17. Since the entrainer 14 moves in relation to the latching part 15 which is connected in a rotationally fixed manner to the injection sleeve 17, the latching increments of the latching installation 35 are perceivable and audible to the operator. The latching installation 35 is effective when setting an amount of injection fluid to be squeezed out.

FIGS. 3 and 4 show the injection device 1 in the injection position 29, after setting an amount of injection fluid to be squeezed out. The operating element 6 here has been rotated by fewer than one full revolution in relation to the upper housing part 3. The injection sleeve 17 in the distal direction has partially moved out of the upper housing part 3. As is shown in FIG. 4, the spring 23 is not only configured as a compression spring, but additionally acts as a torsion spring. To this end, the spring 23 by way of a first end 84 is hooked to the latching part 15, and by way of a second end 85 is hooked to the entrainer 14. The spring 23 is tensioned when the operating element 6 is rotated in the first rotation direction. If and when the operating element 6 between two latching positions of the latching installation 35 is released by the operator, the spring 23 turns the entrainer 14 and, conjointly with the entrainer, the dosing member 18 back to the next lowest latching position, that is, to that latching position which corresponds to the next lowest envisaged amount of injection fluid. Moreover, the spring 23 biases the latching part 15 to the first axial position 88 thereof. The operating element 6 which by way of the latching part 15 is likewise biased to the distal position 90 thereof, bears on the latching part 15.

In order for the set amount of injection fluid to be squeezed out, the operator has to move the operating element 6 in the proximal direction 31, counter to the force of the spring 23 acting in the direction of the longitudinal central axis 50. As is shown in FIG. 4, the operating element 6 has a stop element 32 which in the position shown in FIG. 4 bears on a first stop 33 of the injection sleeve 17. The stop element 32 here bears on the proximal side of the first stop 33, being urged by the spring 23 against the first stop 33. As is also shown in FIG. 4, the injection sleeve 17 has a second stop 34 which is disposed on the proximal side of the stop element 32, in the position shown in FIG. 4 being disposed at a spacing from the stop element 32. As is also shown in FIG. 4, the injection sleeve 17 in the injection position 29 shown in FIG. 4 also bears on a stop 25 of the upper housing part 3, which delimits the maximum amount of injection fluid to be set.

Figure 6:
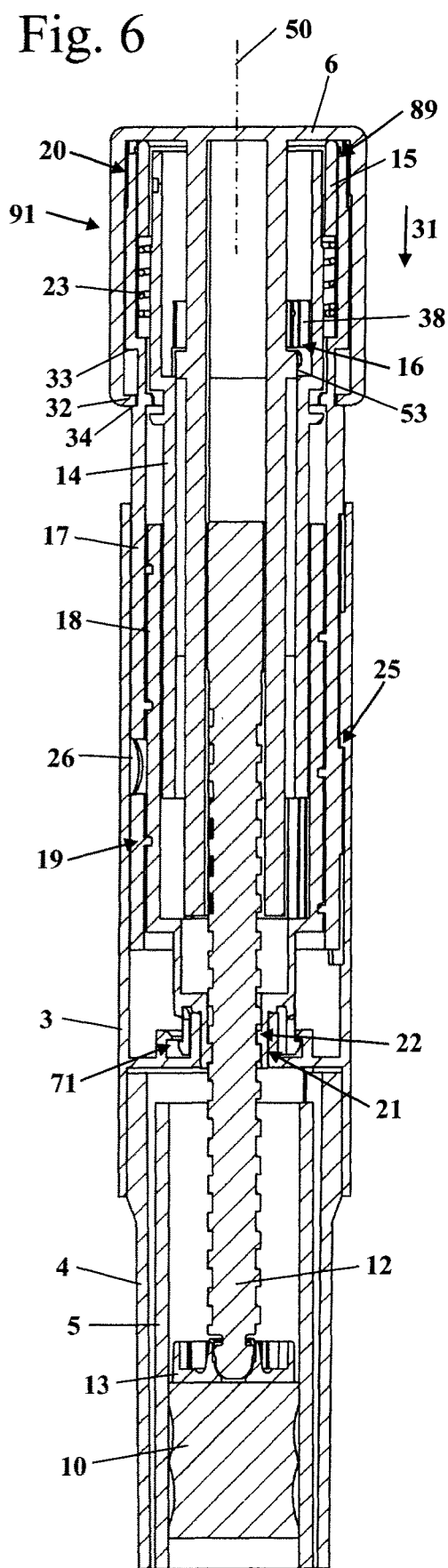
FIG. 6 shows a section along the line VI-VI in FIG. 5.
Figure 28:
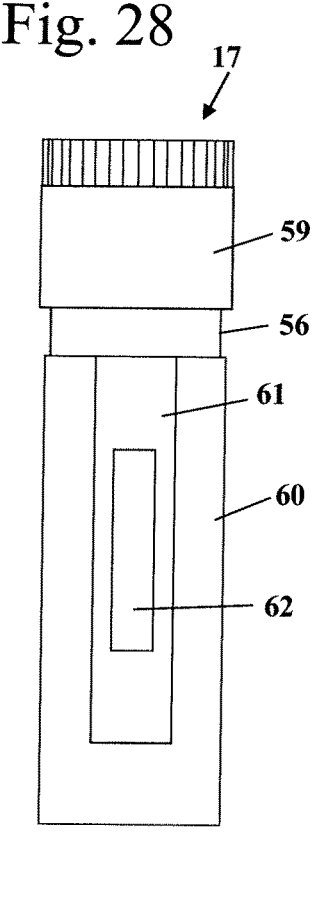
FIGS. 28 and 29 show side views of the injection sleeve.
Figure 29:
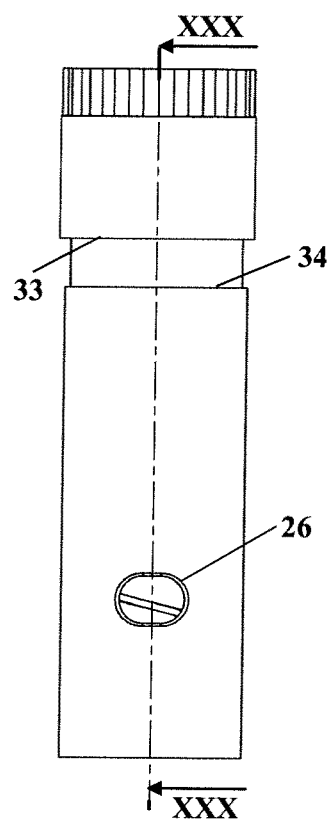
Figure 30:
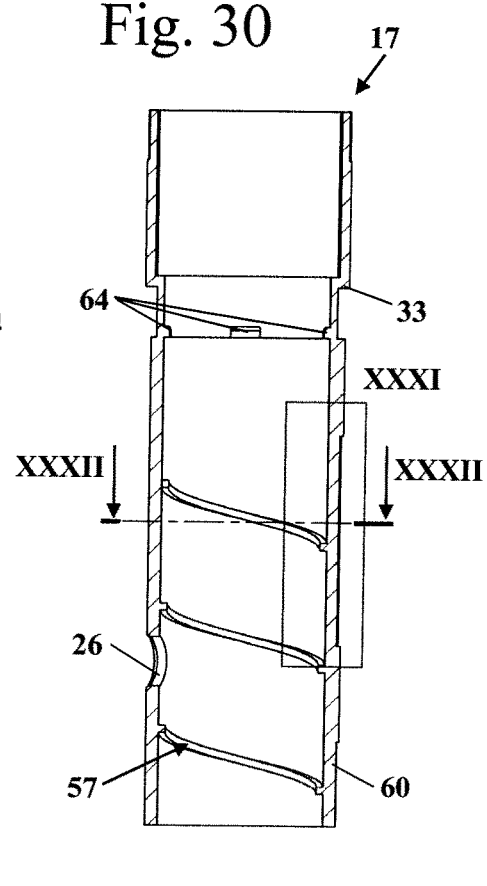
FIG. 30 shows a section along the line XXX-XXX in FIG. 29.
Figure 31:
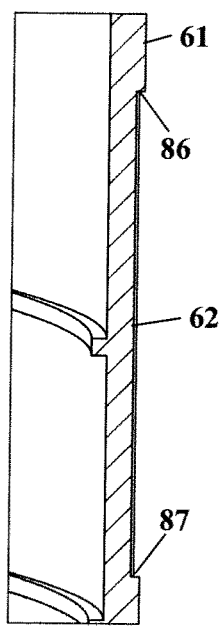
FIG. 31 shows the fragment XXXI of FIG. 30, in an enlarged illustration.
Figure 32:
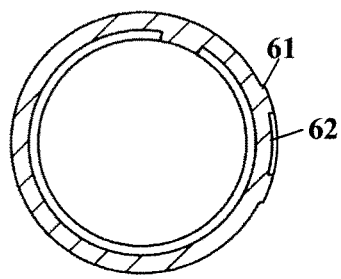
FIG. 32 shows a section along the line XXXII-XXXII in FIG. 30.

FIGS. 5 and 6 show the injection device 1 after displacing the operating element 6 from the distal position 90 thereof to the proximal position 91 thereof, and prior to injection fluid being squeezed out. In the proximal position 91 of the operating element 6, the stop element 32 bears on the second stop 34. As is also shown in FIG. 6, the latching part 15 has been displaced in the proximal direction 31, to the second axial position 89 thereof, by the operating element 6. In this position the latching installation 35 is not active such that no latching positions can be perceived or heard when injection fluid is being squeezed out.

The first coupling 16 is opened in the proximal position 91 of the operating element. As a result the entrainer 14 can rotate in relation to the operating element 6. As is also shown in FIG. 6, the first coupling 16 on the entrainer 14 has latching teeth 38 which in the case of a closed coupling 16 engage between the latching teeth 53 of the operating element 6. In the case of an opened coupling 16, the latching teeth 38 in the direction of the longitudinal central axis 50 are disposed so as to be spaced apart from the latching teeth 53, being mutually disengaged. The second coupling 20 in the proximal position 91 of the operating element 6 is closed such that the operating element 6 is connected in a rotationally fixed manner to the injection sleeve 17 and thus also in a rotationally fixed manner to the upper housing part 3. If and when the operating element 6 is displaced from the position shown in FIG. 6 in the proximal direction 31, the injection sleeve 17 by way of the stop element 32 and by way of the second stop 34 moves in the proximal direction. The dosing member 18 is rotated by way of the first threaded connection 19. The piston rod 12 is connected in a rotationally fixed manner to the operating element 6 and, by way of the operating element 6, in a rotationally fixed manner to the upper housing part 3. By virtue of the rotation of the dosing member 18, the piston rod 12 is moved in the proximal direction, on account thereof squeezing out the set amount of injection fluid from the container 5. The entrainer 14 is entrained by the injection sleeve 17 in the proximal direction. The spring 23 is at least partially relaxed when the operating element 6 moves in the proximal direction 31, on account thereof facilitating the injection procedure.

FIGS. 7 to 10 show the entrainer 14, the latching part 15, and the spring 23. FIG. 8 schematically shows the insertion fit of the two ends 84 and 85 of the spring 23 on the latching part 15 and on the entrainer 14. The latching part 15 has longitudinal grooves 37 for the rotationally fixed connection to the injection sleeve 17. The entrainer 14, on the proximal cylindrical portion thereof, has longitudinal grooves 36 for the rotationally fixed connection to the dosing member 18. This cylindrical proximal region at the distal side thereof is delimited by a periphery 48. As is shown in FIGS. 9 and 10, the entrainer 14 has the inwardly protruding latching teeth 38. The latching teeth 38 do not extend across the entire internal circumference of the entrainer 14. Four groups of three latching teeth 38 each, which are symmetrically disposed, are provided in the embodiment. Another number or arrangement of the latching teeth 38 may also be advantageous. As is also shown in FIGS. 14 and 15, the entrainer 14 has an opening 47, in each case on the proximal side of the latching teeth 38. On account thereof, the proximal end of the latching teeth 38 may be manufactured in a simple manner in terms of production technology. The latching teeth 53 of the operating element 6, which are shown in FIG. 6, in the case of an opened first coupling 16 are located in the region of the openings 47. The spring 23 is configured as a combined compression and torsion spring, biasing the latching part 15 in the distal direction, and biasing the entrainer 14 in the rotation direction about the longitudinal central axis 50 in the direction toward the zero position 28.

FIGS. 9 and 10 also show the latching installation 35 in detail. The latching installation 35 includes a latching element 43 which is configured on the latching part 15. A counter-latching element 40 on the entrainer 14 interacts with the latching element 43. The counter-latching element 40 is configured on a latching arm 39, being resilient by virtue of the inherent elasticity of the material. Both the latching element 43 as well as the counter-latching element 40 in the circumferential direction are asymmetrically configured. The counter-latching element 40 has a latching flank 45, the latching element 43 in the latching position coming to lie there behind. The further flank of the counter-latching element 40 is configured as a guide flank 46 which has a comparatively flat profile. Accordingly, the counter-latching element 40 is also asymmetrically configured, having a latching flank 45 and a guide flank 46. When setting an amount of injection fluid to be squeezed out, the entrainer 14 conjointly with the operating element 6 is rotated in a first rotation direction. The guide flanks 46 come into mutual contact during this rotation. The guide flank 46 of the latching element 43 deflects the counter-latching element 40 in a radially inward manner such that the latching positions can be readily reached. During rotation of the operating element 6 in a second rotation direction, counter to the first rotation direction, the steep latching flanks 45 come into mutual contact. The spring 23 is advantageously conceived such that the force of the spring 23 does not suffice for the latching flanks 45 to be overcome, so that the injection device 1 is always reset to the next lowest latching position when the operating element 6 is released between two latching positions. However, a symmetrical layout of the latching elements 40 and/or 43 may also be advantageous. The latching flanks may be conceived such that the operator may overcome a latching position that has already been reached, being able to reset the operating element 6 to a lower set dosage. The latching flanks may also be conceived such that the latter is impossible.

FIG. 11 shows an opening 94 on the entrainer 14, the second end 85 of the spring 23 (FIG. 8) being hooked into the opening 94. FIGS. 12 and 13 show the configuration of the latching arm 39 which carries the counter-latching element 40. As is also shown in FIG. 13, the periphery 48 delimits the circumferential groove 63, the retaining periphery 64 of the injection sleeve 17 (FIG. 2) protruding thereinto.

FIGS. 16 to 19 show the latching part 15. As is shown in particular in FIG. 19, the latching part 15 for the rotationally fixed connection to the injection sleeve 17 has on the external circumference two longitudinal grooves 37, disposed so as to be mutually opposite. Four latching elements 41, 42, 43, and 44, which are of identical configuration and are disposed at dissimilar mutual spacings on the circumference, are configured on the latching part 15 in the embodiment. The latching element 41 corresponds to the zero position, the latching element 42 is assigned to the priming position, the latching element 43 is assigned to a first dosage, and the latching element 44 is assigned to a second dosage. The latching part 15 at the distal end side 49 thereof is configured in a rounded manner. The latching part 15, by way of this end side 49, bears on the operating element 6. Low friction forces result by way of the rounded configuration when the operating element 6 is being rotated in relation to the latching part 15.

FIGS. 20 to 24 show the operating element 6. As is shown in FIGS. 20 and 21, the entrainment portion 51 of the operating element 6, by way of which the operating element 6 is connected in a rotationally fixed manner to the piston rod 12 (FIG. 1), is configured by two arms 52 which extend in the longitudinal direction of the injection device 1. As is shown in FIG. 23, the operating element 6, in the distal region of the circumferential wall thereof, carries an internal toothing 54 which interacts with a toothing 55, shown in FIG. 25, on the external circumference of the injection sleeve 17, forming with the latter the second coupling 20. As is shown in FIG. 24, the latching teeth 53 which together with the latching teeth 38 of the entrainer 14 form the first coupling 16, are likewise not distributed across the entire circumference of the operating element 6, but are in each case only disposed in part-regions. The latching teeth 53 and the latching teeth 38 are to be disposed such that it is ensured in every rotational position of the operating element 6 in relation to the entrainer 14 that at least one latching tooth 50 engages with at least one latching tooth 38. As is shown in FIGS. 23 and 24, the stop element 32 is configured as an inwardly protruding periphery. No continuous periphery is provided in the embodiment; rather, four individual and mutually separated peripheral portions which form stop elements 32 are provided. During assembly of the operating element the stop elements 32 snap-fit behind the first stop 33 of the injection sleeve 17. However, a continuous stop element 32 which extends across the entire circumference may also be advantageous.

The injection sleeve 17 is shown in FIGS. 25 to 32. The injection sleeve 17 is configured in the shape of a sleeve, having a distal portion 59 and a proximal portion 60 which are mutually separated by a groove 56. The stops 33 and 34 are configured on those sides that delimit the groove 56. The stop elements 32 of the operating element 6 protrude into the groove 56. The injection sleeve 17 on the internal side thereof has two longitudinal webs 58, shown in FIG. 26, which serve for the rotationally fixed connection to the latching part 15 and which protrude into the longitudinal grooves 37 of the latching part 15. The opening 26 through which the outside of the dosing member 18 is visible to the operator is also shown in FIGS. 25 and 26. As is shown in FIGS. 28 and 30 to 32, the proximal portion 60 of the injection sleeve 17, on that side that is opposite the opening 26, has a longitudinal web 61 which is configured as an elevation on the external circumference. The longitudinal web 61 has a rectangular depression 62. The configuration of the depression 62 is shown in detail in FIG. 31.

The depression 62 has a distal edge 86 which in the zero position 28 of the injection device 1 interacts with a distal edge 78, shown in FIG. 42, on the upper housing part 3, forming with the distal edge 78 the first stop 24. The depression 62 has a proximal edge 87 which in the injection position 29, shown in FIG. 4, which corresponds to the maximum settable amount of injection fluid to be squeezed out, bears on a proximal edge 79 of the upper housing part 3 (FIG. 42), forming with the proximal edge 79 the second stop 25. The second stop 25 delimits the maximum settable amount of injection fluid to be squeezed out.

As is shown in FIGS. 42 and 43, the upper housing part 3 has a depression 76 which is configured as an approximately rectangular longitudinal groove, a longitudinal web 77 rising therefrom. The longitudinal web 61 of the injection sleeve 17 protrudes into the depression 76. On account thereof, the injection sleeve 17 in the circumferential direction is secured against rotating in relation to the housing 2. The longitudinal web 77 of the upper housing part 3 protrudes into the depression 62 of the injection sleeve 17, forming with the depression the stops 24 and 25. The longitudinal web 77 and the depression 62 also form an anti-rotation security feature for the injection sleeve 17. As is shown in particular in FIG. 30, the injection sleeve 17 in the proximal portion 60 thereof carries an internal thread 57.

Figure 33:
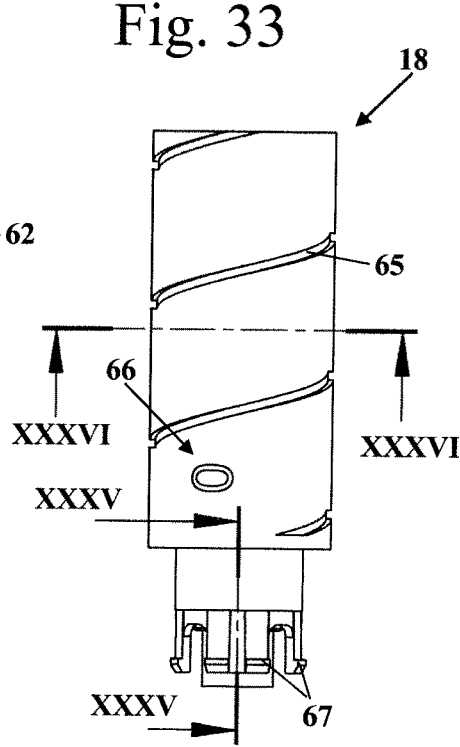
FIGS. 33 and 34 show side views of the dosing member.
Figure 34:
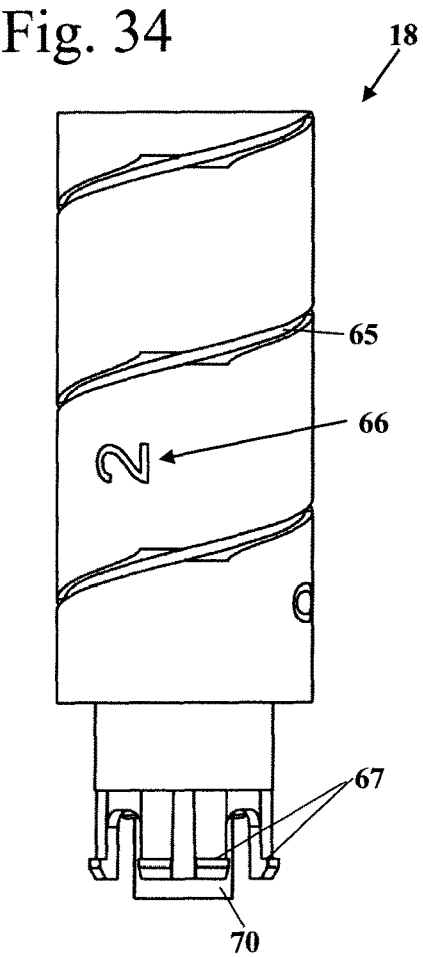
Figure 35:
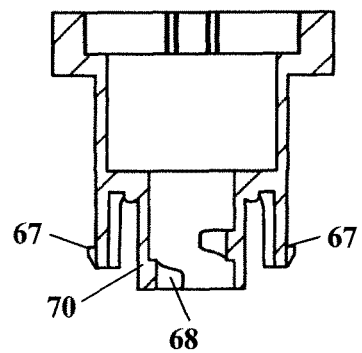
FIG. 35 shows a section along the line XXXV-XXXV in FIG. 33.
Figure 36:
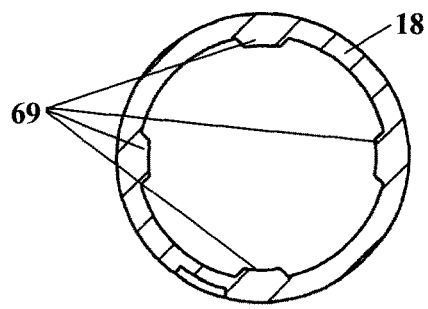
FIG. 36 shows a section along the line XXXVI-XXXVI in FIG. 33.

The dosing member 18 is shown in detail in FIGS. 33 to 36. The dosing member 18 on the external side thereof carries an external thread 65 which with the internal thread 57 of the injection sleeve 17 (FIG. 30) forms the first threaded connection 19. The dosing member 18, in the region of the external thread 65, has the graduation 66, shown in FIGS. 33 and 34, which indicates to the operator the set amount of injection fluid. As is shown in FIGS. 33 to 35, the dosing member 18 on the proximal side thereof has latching hooks 67. As is shown in FIG. 42, the upper housing part 3 has an encircling latching periphery 75, the latching hooks 67 hooking thereinto and thus forming the latching connection 71. As is shown in FIGS. 34 and 35, the dosing member 18 on the proximal side thereof has a mounting pin 70 which is mounted in a bearing sleeve 74 of the upper housing part 3 (FIG. 42). On account thereof, the dosing member 18 is rotatably mounted in the upper housing part 3. As is shown in FIG. 35, an internal thread 68 is disposed in the mounting pin 70. The internal thread 68 interacts with the external thread 92 of the piston rod 12, shown in FIGS. 37 and 38, and with the latter forms the second threaded connection 22. As is shown in FIG. 36, the substantially sleeve-shaped dosing member 18, on the internal circumference thereof, has a total of four longitudinal webs 69 which serve for the rotationally fixed connection to the entrainer 14. To this end, the longitudinal webs 69 protrude into the longitudinal grooves 36 of the entrainer 14, which are shown in FIGS. 11 to 13.

Figure 37:
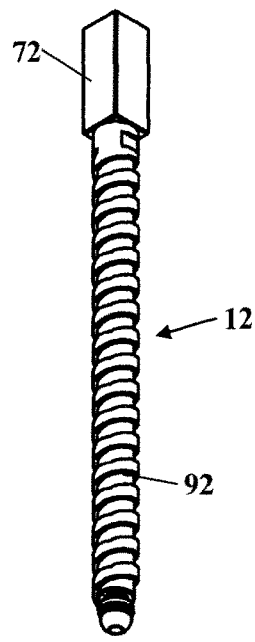
FIG. 37 shows a perspective illustration of a piston rod of the injection device of FIGS. 1 to 6.
Figure 38:
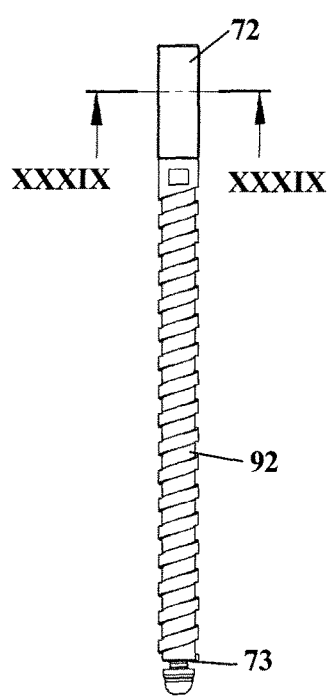
FIG. 38 shows a side view of the piston rod of FIG. 37.
Figure 39:
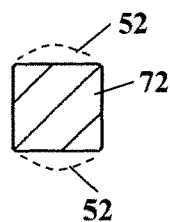
FIG. 39 shows a section along the line XXXIX-XXXIX in FIG. 38.

As is shown in FIGS. 37 to 39, the piston rod 12 on the distal side thereof has a guide portion 72 which has a rectangular cross section which in the embodiment is square. The arms 52 of the operating element 6, which are schematically indicated in FIG. 39, bear on opposite longitudinal sides of the guide portion 72, on account thereof producing a rotationally fixed connection between the operating element 6 and the piston rod 12. The piston rod 12, on the proximal region thereof, has a groove 73 to which the piston disk 13 is hooked (FIG. 2).

As is shown in FIG. 42, the upper housing part 3, in the proximal region thereof, has latching hooks 80 which serve for the latching connection to the holder 4 which is shown in FIGS. 44 and 45. The holder 4 in the distal region thereof has latching openings 81 into which the latching hooks 80 hook. Two latching hooks 80 and two latching openings 81 are shown in the embodiment. The latching installation 9 is also shown in FIGS. 44 and 45. The latching installation 9 is formed by two mutually opposite latching hooks 82 which latch onto the container 5. The holder 4, on the external circumference thereof, in the proximal region has an external thread 83 onto which the injection needle 8 (FIG. 1) is screwed.

Figure 46:
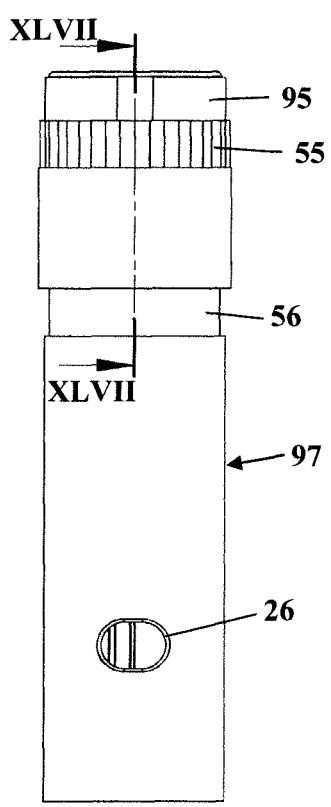
FIG. 46 shows an injection sleeve, a latching part, and an entrainer of an embodiment of an injection device.
Figure 47:
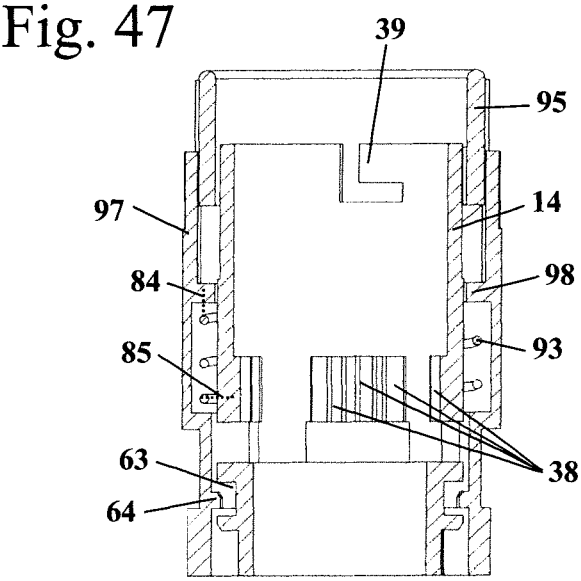
FIG. 47 shows a section along the line XLVII-XLVII in FIG. 46.
Figure 48:
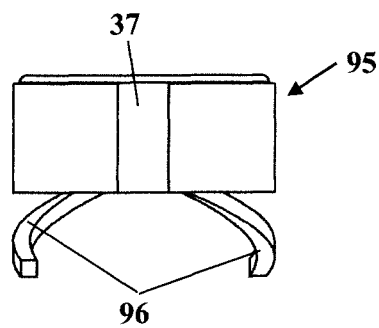
FIGS. 48 to 52 show perspective illustrations of the latching part of FIGS. 46 and 47.
Figure 49:
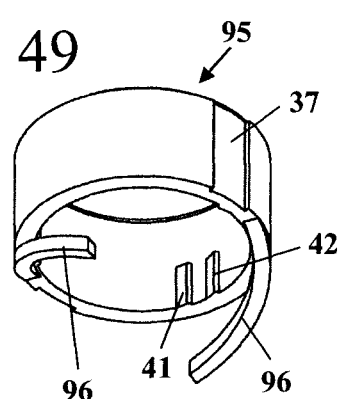
Figure 50:
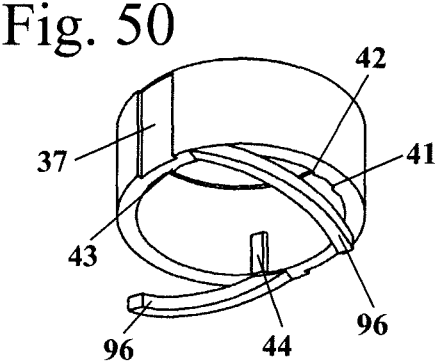
Figure 51:
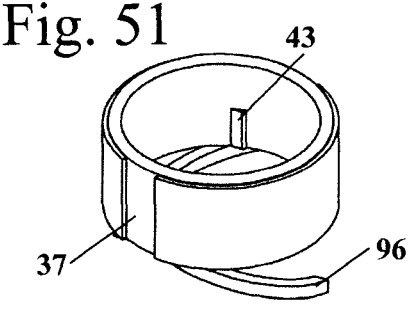
Figure 52:
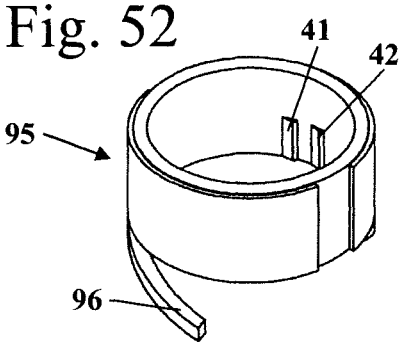
Figure 53:
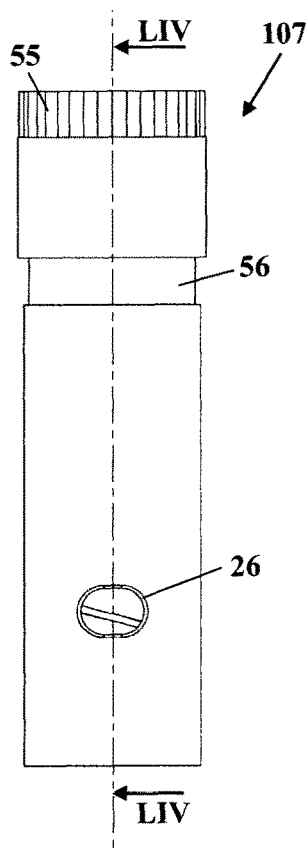
FIG. 53 shows a side view of an embodiment of an injection sleeve of an injection device.

In the embodiment as per FIGS. 1 to 45 the spring 23 fulfills a dual function, since the former has to both generate torque between the entrainer 14 and the latching part 15 as well as bias the latching part 15 and the operating element 6 in the distal direction. In order for the layout of the spring 23 to be simplified, separate spring elements may be provided for generating the axial force and for generating the torque. A respective embodiment is shown in FIGS. 46 to 52. The same reference signs are used for designating corresponding elements in all figures of the present application. An injection sleeve 97 in which a latching part 95 and an entrainer 14 are disposed is shown in FIGS. 46 and 47. The injection sleeve 97 has an inwardly protruding support periphery 98 on which a first end 84 of a spring 93 is secured. A second end 85 of the spring 93 is hooked to the entrainer 14. The spring 93 serves for generating torque between the injection sleeve 97 and the entrainer 14. Since the entrainer 14 is connected in a rotationally fixed manner to the dosing member 18, the torque acts between the dosing member 18 and the injection sleeve 97, biasing the dosing member 18 in the direction toward the zero position 28 of the assembly.

As is shown in FIGS. 48 to 52, the latching part 95, on the proximal side thereof, has two spring arms 96. In the embodiment the spring arms 96 are configured preferably from plastics so as to be integral with the latching part 95. By virtue of the inherent elasticity thereof, the spring arms 96 bias the latching part 95 in the distal direction. Instead of the spring arms 96, a screw compression spring or a spring element of another configuration may also be expedient for biasing the latching part 95 and the operating element 6 in the direction of the longitudinal central axis 50.

Figure 54:
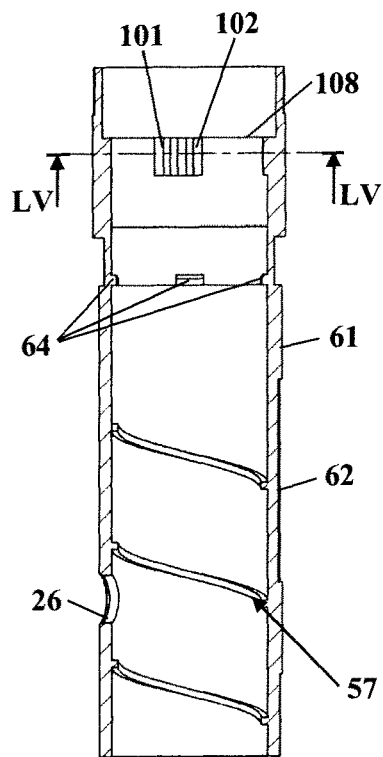
FIG. 54 shows a section along the line LIV-LIV in FIG. 53.

A further embodiment of an injection device is shown in FIGS. 53 to 58, wherein only the injection sleeve 107 and the entrainer 114 are shown. The further elements which are not shown correspond to the components which are shown and described in the context of the injection device 1. As is shown in FIG. 54, the injection sleeve 107, on the internal circumference thereof, has latching elements 101, 102, 103, and 104. The latching elements 101, 102, 103, and 104 establish the latching positions of the injection device 1. As is shown in FIG. 54, the latching elements 101 to 104 on the circumference have dissimilar mutual spacings. The latching element 101 is assigned to the zero position, the latching element 102 is assigned to the priming position, and the latching elements 103 and 104 are assigned to a first and second amount of injection fluid to be squeezed out.

Figure 55:
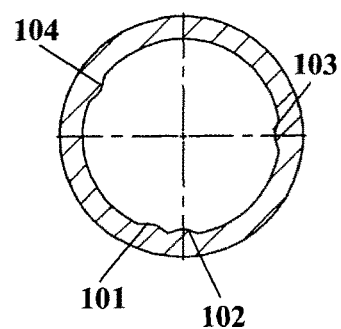
FIG. 55 shows a section along the line LV-LV in FIG. 54.
Figure 56:
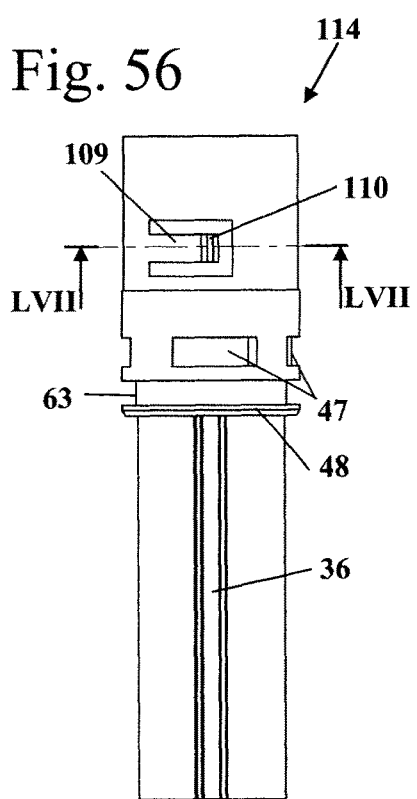
FIG. 56 shows a side view of an embodiment of an entrainer of an injection device.
Figure 57:
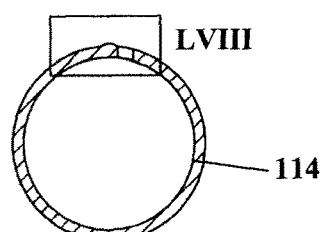
FIG. 57 shows a section along the line LVII-LVII in FIG. 56.
Figure 58:
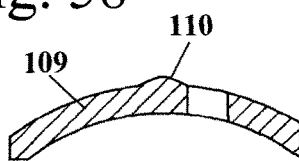
FIG. 58 shows the fragment LVIII in FIG. 57, in an enlarged illustration.

As is shown in FIGS. 56 to 58, the entrainer 114 has a latching arm 109 on which a counter-latching element 110 is configured which, for defining the latching positions, may interact with the latching elements 101 to 104. Since the relative position of the injection sleeve 107 and of the entrainer 114 by virtue of the retaining peripheries 64 which protrude into the circumferential groove 63 is predefined, the latching installation which is formed by the latching elements 101 to 104 and the counter-latching element 110 is effective both when setting an amount of injection fluid to be squeezed out and when squeezing out the injection fluid from the container. As is shown in FIGS. 55 and 58, the latching elements 101 to 104 and the counter-latching element 110 in the circumferential direction are configured so as to be approximately symmetrical such that no excessive force is required in order to overcome the latching positions when the injection fluid is being squeezed out. In the case of the injection device which is shown in FIGS. 53 to 58, no spring is provided which biases the dosing member in the direction of the zero position. A step 108 for bearing a compression spring which acts between the injection sleeve 107 and an operating element (not shown in FIGS. 53 to 58) and which biases the operating element in the distal direction is provided on the internal circumference of the injection sleeve 107.

A further embodiment of an injection device 121 is shown in FIGS. 59 to 62. The injection device 121 has an upper housing part 123, a latching arm 129 being configured thereon. The latching arm 129 in the embodiment is visible from the outside. However, the latching arm 129 is advantageously configured such that the former is invisible to the operator. The injection device 121 has an injection sleeve 127 which substantially corresponds to the injection sleeve 17 of the injection device 1. However, the injection sleeve 127, on the external side thereof, has latching elements 128 which are configured as depressions and into which a counter-latching element 130 which is configured on the latching arm 129 and which in the embodiment is configured as a latch can latch, so as to form with the latching elements 128 a latching installation 125. As is shown in FIG. 61, the injection device 121 has an entrainer 124 which does not carry any latching elements or counter-latching elements. A latching part is also not provided. A spring 133 which biases the operating element 6 in the distal direction is disposed in the operating element 6. In the embodiment, the latching installation 125 acts between the upper housing part 123 and the injection sleeve 127 both when setting an amount of injection fluid to be squeezed out, as well as when the injection fluid is being squeezed out of the container 5. However, it may also be provided that the latching arm 129, when the operating element 6 is being readjusted to the proximal position 91 thereof (FIG. 6), is deflected such that the counter-latching element 130 cannot interact with the latching elements 128. This is expedient in particular when the latching arm 129 is disposed not on the upper housing part 123 but on the injection sleeve 127, the latching elements 128 being disposed on the upper housing part 123.

Figure 62:
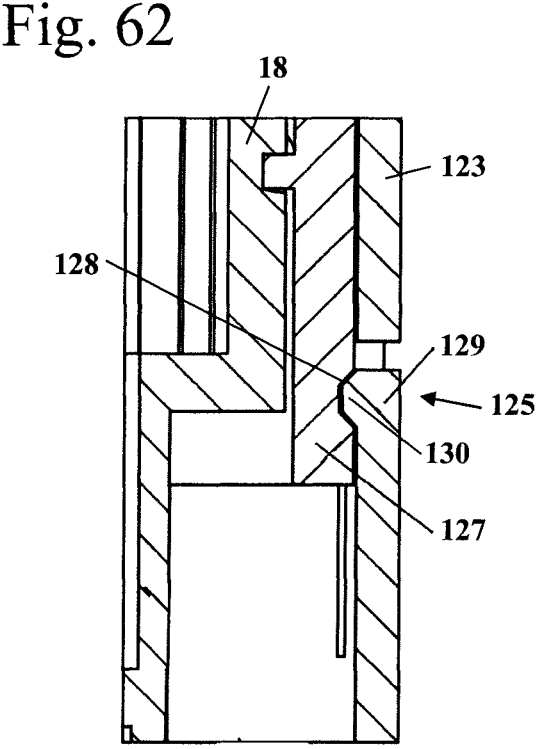
FIG. 62 shows the fragment LXII in FIG. 61, in an enlarged illustration.
Figure 63:
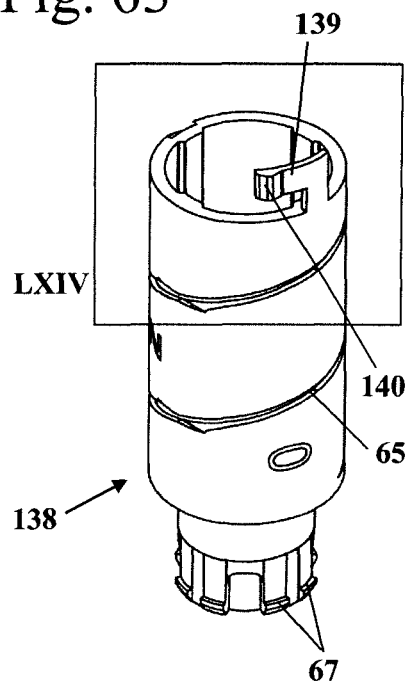
FIG. 63 shows a perspective illustration of an embodiment of a dosing member.
Figure 64:
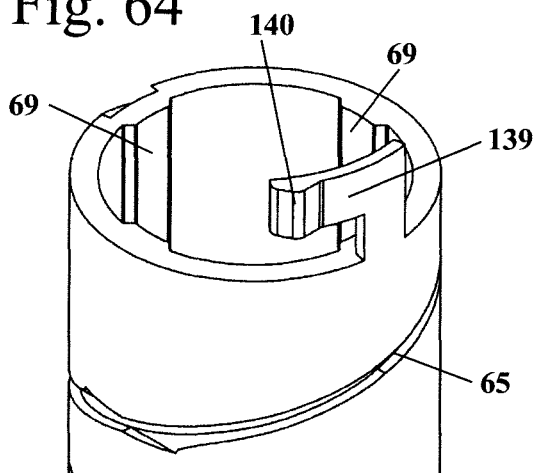
FIG. 64 shows the fragment LXIV of FIG. 63, in an enlarged illustration.
Figure 65:
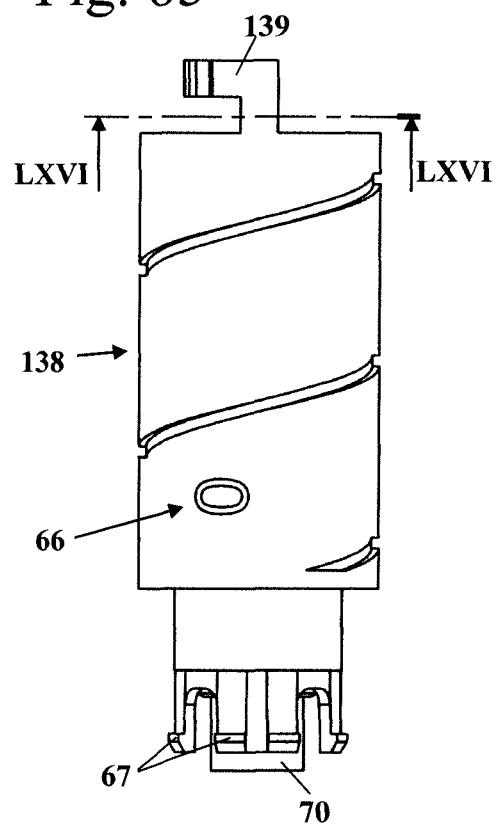
FIG. 65 shows a side view of the dosing member of FIG. 63.

In the case of the injection device 121 shown in FIGS. 59 to 62, a spring which biases the dosing member in the second rotation direction and which acts between the injection sleeve 127 and the dosing member may also be provided. As is shown in FIG. 62, the latching element 128 and the counter-latching element 130 in the embodiment shown are symmetrically embodied. If and when a spring is additionally provided for biasing the dosing member in the second rotation direction, it may be expedient for the latching elements to be asymmetrically configured such that dissimilar forces for overcoming the latching positions when setting and when squeezing out the injection fluid result, the additional spring in each case being able to turn back the dosing member only to the next lowest envisaged amount of injection fluid.

Figure 66:
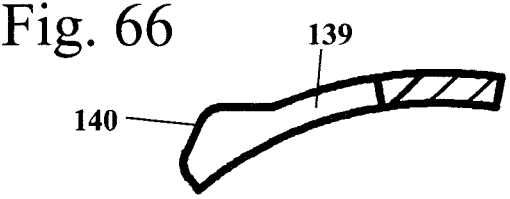
FIG. 66 shows a section along the line LXVI-LXVI in FIG. 65.

A further embodiment of an injection device 131 (FIGS. 70 and 72) is shown in FIGS. 63 to 73. The dosing member 138 of the injection device 131 is shown in FIGS. 63 to 66. The dosing member 138 on the distal side thereof has a latching arm 139 which carries a counter-latching element 140. The further construction of the dosing member 138 corresponds substantially to the construction of the dosing member 18. As is shown in FIG. 66, the counter-latching element 140 in the embodiment is symmetrically configured. As is shown in FIGS. 67 to 69, the injection device 131 has an injection sleeve 137 which, on the internal circumference thereof, carries latching elements 141 and 142. The latching elements 141 and 142 in the embodiment are configured as depressions. Further latching elements may be provided. It may be advantageous for the latching arm 139 to be configured on the injection sleeve 137 instead of on the dosing member 138, and for corresponding latching elements or latching depressions to be provided on the dosing member 138. The latching elements 141 and 142 are mutually offset both in the direction of the longitudinal central axis 50 as well as in the circumferential direction. The latching elements 141 and 142 lie on a helical path which corresponds to the thread pitch of the external thread 65 of the dosing member 138. On account of the latching elements 141 and 142 being mutually offset both in the direction of the longitudinal central axis 50 as well as in the circumferential direction, comparatively minor spacings between the latching positions are possible.

Figure 72:
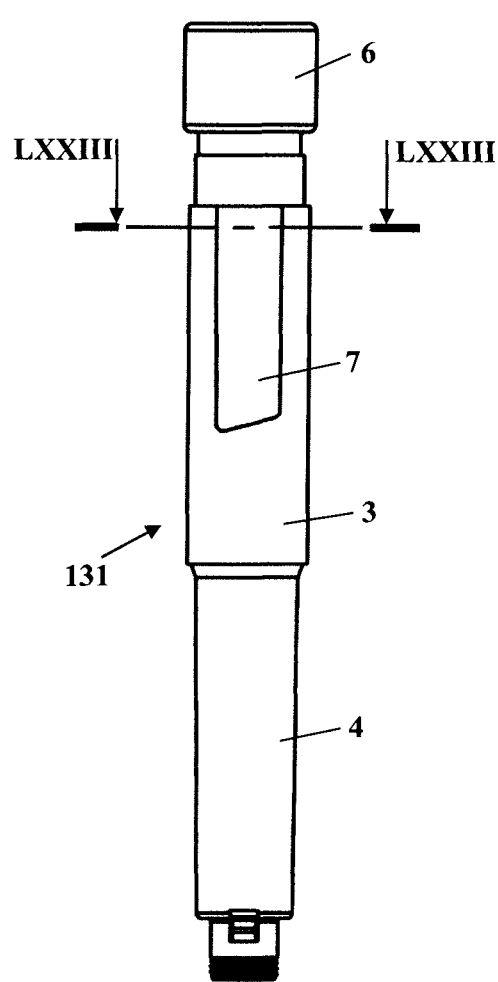
FIG. 72 shows a side view of the injection device of FIG. 70 after setting an amount of injection fluid to be squeezed out.
Figure 73:
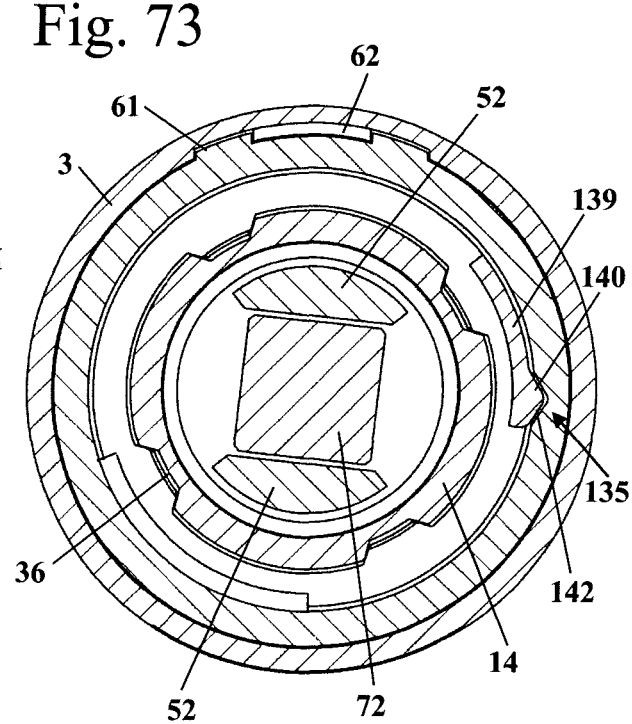
FIG. 73 shows a section along the line LXXIII-LXXIII in FIG. 72.

The injection device 131 is shown in the zero position in FIGS. 70 and 71. The latching element 141 is latched to the counter-latching element 140, forming with the latter a latching installation 135. The injection device 131 in FIGS. 72 and 73 is located in an injection position. The counter-latching element 140 is latched to the latching element 142. By virtue of the symmetrical configuration of the latching elements 141, 142, and of the counter-latching element 140, the latching positions in both rotation directions may readily be bridged by the operator, so that the operator may reset the injection device 131 from an already set dosage to the zero position, without injection fluid being squeezed out. However, another asymmetrical layout of the latching elements may also be expedient. A spring which biases the dosing member 138 in the second rotation direction may also be provided between the injection sleeve 137 and the dosing member 138 in the case of the embodiments of an injection device 131 shown in FIGS. 63 to 73. Since the injection sleeve 137 in relation to the dosing member 138 moves not only in the circumferential direction but also in the axial direction, a set amount of injection fluid is unequivocally assigned to each relative position of the injection sleeve 137 and of the dosing member 138, even in the case of a plurality of revolutions of the operating element 6 up to the maximum dosage.

It is understood that the foregoing description is that of the preferred embodiments of the invention and that various changes and modifications may be made thereto without departing from the spirit and scope of the invention as defined in the appended claims.

What is claimed is:

1. An injection device defining a longitudinal center axis, a proximal direction and a distal direction, the injection device comprising:
   a housing;
   a dosing member held so as to be rotatable and fixed in said housing in the direction of the longitudinal center axis;
   an injection sleeve held so as to be rotationally fixed in relation to said housing and displaceable in the direction of said longitudinal center axis;
   said dosing member being connected to said injection sleeve via a first threaded connection;
   said dosing member being configured to rotate in a first rotational direction in relation to said housing when an amount of injection fluid to be dispensed is being set;
   said injection sleeve being configured to move in the distal direction because of said first threaded connection;
   said dosing member being further configured to rotate in a second rotational direction counter to said first rotational direction when said amount of injection fluid to be dispensed is being pressed out;
   said injection sleeve being configured to move in the proximal direction because of said first threaded connection;
   a container configured to contain injection fluid;
   a dosing piston configured to press injection fluid out of said container;
   said dosing piston being connected to said dosing member via a second threaded connection;
   said dosing piston being connected to said dosing member in a rotationally fixed manner so as to rotate conjointly therewith when said amount of injection fluid to be dispensed is being set;
   said dosing piston being connected to said injection sleeve in a rotationally fixed manner when said amount of injection fluid to be dispensed is pressed out and, by virtue of said second threaded connection, is moved in the proximal direction;
   a latching unit configured to act at least when said amount of injection fluid to be dispensed from said container is being set, where said latching unit has a latching element and a counter-latching element configured to interact with the latching element in a latching position; and, said latching unit being configured to act between the injection sleeve and dosing member which, during setting of the amount of injection fluid to be dispensed, move relative to one another, wherein a set amount of injection fluid is unequivocally assigned to each relative mutual position of the injection sleeve and the dosing member, wherein a latching part is connected with one of the dosing member and the injection sleeve in a rotatably fixed manner and such that the latching part is displaceable relative to the one of the dosing member and the injection sleeve, and wherein the latching element being arranged on the latching part.

2. The injection device of claim 1 further comprising:
a first coupling;
an entrainer connected to said dosing member in a rotationally fixed manner;
a second coupling;
an operating element configured to be connectable to said entrainer in a rotationally fixed manner via said first coupling and to be connectable to said injection sleeve via said second coupling;
said operating element having a distal position and a proximal position in relation to said injection sleeve;
said operating element being configured to be connected to said entrainer in a rotationally fixed manner via said first coupling when said operating element is in said distal position;
said second coupling being open when said operating element is in said distal position so as to enable said operating element to rotate in relation to said injection sleeve;
said first coupling being configured to be open when said operating element is in said proximal position;
said operating element being configured to be rotatable in relation to said entrainer and to be connected to said injection sleeve in a rotationally fixed manner via said second coupling when said operating element is in said proximal position.

3. The injection device of claim 2, wherein said latching unit is active when said operating element is in said distal position.

4. The injection device of claim 2, wherein said entrainer is, in the direction of the longitudinal center axis, coupled to a position of said injection sleeve.

5. The injection device of claim 2, wherein said latching part is in the second axial position when the operating element is in the proximal position.

6. The injection device of claim 1, wherein said latching part is biased in the direction of said first axial position.

7. The injection device of claim 6, wherein said latching part includes at least one spring arm configured to bias said latching part in the direction of said first axial position.

8. The injection device of claim 1 further comprising a spring configured to act between said injection sleeve and said dosing member and to bias said dosing member in said second rotational direction.

9. The injection device of claim 8 wherein said spring has a first end fixed on said injection sleeve and a second end fixed on said entrainer.

10. The injection device of claim 1, wherein the latching element is configured to be able to engage the counter-latching element in a first axial position of the latching part and to be disengaged from the counter-latching element in a second axial position of the latching part independent of the relative mutual position of the entrainer and the injection sleeve.

* * * * *